United States Patent
Michrowska-Pianowska et al.

(10) Patent No.: US 9,750,256 B2
(45) Date of Patent: *Sep. 5, 2017

(54) HERBICIDAL ISOXAZOLO[5,4-B]PYRIDINES

(71) Applicant: BASF SE, Ludwigshafen (DE)

(72) Inventors: Anna Aleksandra Michrowska-Pianowska, Mannheim (DE); Markus Kordes, Frankenthal (DE); Johannes Hutzler, Waldsee (DE); Trevor William Newton, Neustadt (DE); Richard Roger Evans, Limburgerhof (DE); Klaus Kreuz, Denzlingen (DE); Klaus Grossmann, Tuebingen (DE); Thomas Seitz, Viernheim (DE); Andree van der Kloet, Arnhem (NL); Matthias Witschel, Bad Duerkheim (DE); Liliana Parra Rapado, Offenburg (DE); Jens Lerchl, Golm (DE)

(73) Assignee: BASF SE, Ludwigshafen (DE)

( * ) Notice: Subject to any disclaimer, the term of this patent is extended or adjusted under 35 U.S.C. 154(b) by 159 days.

This patent is subject to a terminal disclaimer.

(21) Appl. No.: 14/371,620

(22) PCT Filed: Jan. 4, 2013

(86) PCT No.: PCT/EP2013/050080
§ 371 (c)(1),
(2) Date: Jul. 10, 2014

(87) PCT Pub. No.: WO2013/104561
PCT Pub. Date: Jul. 18, 2013

(65) Prior Publication Data
US 2015/0038332 A1    Feb. 5, 2015

Related U.S. Application Data

(60) Provisional application No. 61/585,718, filed on Jan. 12, 2012.

(51) Int. Cl.
*A01N 43/90* (2006.01)
*C07D 498/04* (2006.01)

(52) U.S. Cl.
CPC .......... *A01N 43/90* (2013.01); *C07D 498/04* (2013.01)

(58) Field of Classification Search
None
See application file for complete search history.

(56) References Cited

U.S. PATENT DOCUMENTS

| 3,541,101 A | 11/1970 | Markillie et al. |
| 5,510,319 A | 4/1996 | Cross et al. |
| 6,683,027 B2 | 1/2004 | Baltruschat et al. |
| 8,148,380 B2 | 4/2012 | Guiles et al. |
| 8,618,179 B2 | 12/2013 | Klingelhoefer et al. |
| 9,131,695 B2* | 9/2015 | Michrowska-Pianowska ............... A01N 43/90 |
| 2009/0163545 A1 | 6/2009 | Goldfarb |
| 2014/0080701 A1 | 3/2014 | Klingelhoefer et al. |
| 2014/0243201 A1 | 8/2014 | Klingelhoefer et al. |
| 2016/0037776 A1* | 2/2016 | Michrowska-Pianowska ............... A01N 43/90 504/225 |
| 2016/0037777 A1* | 2/2016 | Michrowska-Pianowska ............... A01N 43/90 504/105 |

FOREIGN PATENT DOCUMENTS

| WO | WO 2009/015208 | 1/2009 |
| WO | WO 2011/086115 | 7/2011 |
| WO | WO 2011/101303 | 8/2011 |
| WO | WO 2011/113786 | 9/2011 |
| WO | WO 2011/117151 | 9/2011 |
| WO | WO 2011/117152 | 9/2011 |
| WO | WO 2011/117195 | 9/2011 |
| WO | WO 2011/117211 | 9/2011 |
| WO | WO 2012/010633 | 1/2012 |
| WO | WO 2012/041789 | 4/2012 |

OTHER PUBLICATIONS

International Search Report dated Feb. 19, 2013, prepared in International Application No. PCT/EP2013/050080.
International Preliminary Report on Patentability dated Jul. 15, 2014, prepared in International Application No. PCT/EP2013/050080.
Database Registry [Online] Chemical Abstracts Service, Columbus Ohio, US, 2008, XP002660620, retrieved from STN, Database Accession No. 1061838-57-0 compounds 1061838-57-0, Nov. 19, 2012.
Database Registry [Online] Chemical Abstracts Service, Columbus Ohio, US, 2008, XP002660621, retrieved from STN, Database Accession No. 1099890-46-0 compounds 1099890-46-0, Nov. 19, 2012.
Elbannany, Afaf A., "Synthesis of new isoxazolo[4,3-b]pyridine derivatives", Pharmazie, 1988, p. 128-129, vol. 43.
Volochnyuk, Dmitriy et al. "Approach to the Library of Fused Pyridine-4-carboxylic Acids by Combes-Type Reaction of Acyl Pyruvates and Electron-Rich Amino Heterocycles", J. Comb. Chem, 2010, p. 510-517, vol. 12.

(Continued)

*Primary Examiner* — Mina Haghighatian
*Assistant Examiner* — Erin Hirt
(74) *Attorney, Agent, or Firm* — Brinks Gilson & Lione

(57) ABSTRACT

The invention relates to isoxazolo[5,4-b]pyridine compounds of formula I,

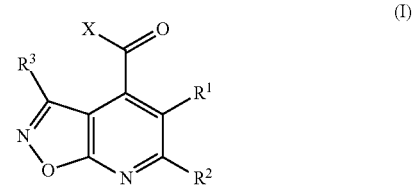

to the agriculturally useful salts of isoxazolo[5,4-b]pyridine compounds of formula I, and to their use as herbicides.

22 Claims, No Drawings

(56) References Cited

OTHER PUBLICATIONS

Office Action dated Mar. 5, 2014 in corresponding U.S. Appl. No. 13/811,095.
Office Action dated Sep. 16, 2014 in corresponding U.S. Appl. No. 13/811,095.
Final Office Action dated Oct. 6, 2016 from U.S. Appl. No. 14/828,104, filed Aug. 17, 2015.

* cited by examiner

HERBICIDAL ISOXAZOLO[5,4-B]PYRIDINES

The present invention relates to isoxazolo[5,4-b]pyridines of general formula I as defined below and to their use as herbicides. Moreover, the invention relates to compositions for crop protection and to a method for controlling unwanted vegetation.

Compounds having an isoxazolo[5,4-b]pyridine moiety are known in the art. US2009/163545 describes such compounds as lifespan-altering for eukaryotic organisms. According to WO2009/015208, particular urea derivatives show an antibacterial effect. Potential routes for synthesis of isoxazolo[5,4-b]pyridine compounds are known from Elbannany et al, Pharmazie (1988) 43(2), 128-129 and Volochnyuk et al, Journal of Combinatorial Chemistry (2010) 12(4), 510-517.

WO2012/010633 discloses certain isoxazolo[5,4-b]pyridine compounds and their use as herbicides. U.S. Pat. No. 5,510,319 describes certain isoxazolo[5,4-b]pyridine compounds with carboxylic functionality.

In agriculture, there is a constant demand to develop novel active ingredients, which complement or outperform present methods of treatment regarding activity, selectivity and environmental safety.

It is therefore an object of the present invention to provide chemical compounds, which are suitable as herbicides. In particular, it is an object to identify chemical compounds with high herbicidal activity, preferably at low application rates, while leaving desirable plants, e.g. crop plants, unharmed.

These and further objects are achieved by isoxazolo[5,4-b]pyridines of formula I as defined below and by their agriculturally useful salts.

Accordingly, the present invention provides isoxazolo[5,4-b]pyridines of formula I

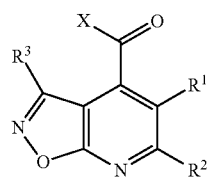

I where in formula I, the variables are as defined below:

$R^1$ hydrogen, halogen, hydroxyl, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_3$-$C_6$-halocycloalkyl, $C_2$-$C_6$-alkenyl, $C_2$-$C_6$-alkynyl, $C_1$-$C_6$-alkoxy, $C_1$-$C_6$-haloalkoxy, phenyl, phenyl-$C_1$-$C_6$-alkyl;

$R^2$ hydrogen, $C_1$-$C_6$-alkyl, $C_1$-$C_6$-haloalkyl, $C_1$-$C_6$-hydroxyalkyl, $C_1$-$C_6$-alkoxy-$C_1$-$C_6$-alkyl, $C_3$-$C_6$-cycloalkyl, $C_3$-$C_6$-halocycloalkyl, $C_1$-$C_6$-alkyl-$C_3$-$C_6$-cycloalkyl, phenyl-$C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, amino, $C_1$-$C_6$-alkylamino, N,N-di-($C_1$-$C_6$-alkyl)amino, heterocyclyl, phenyl; wherein the heterocyclyl and phenyl moieties of $R^2$ can be unsubstituted or substituted with one or more radicals selected from halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;

or $R^1$ and $R^2$ together form an $C_3$-$C_5$-alkanediyl;

$R^3$ $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, $C_3$-$C_6$-cycloalkylthio, $C_3$-$C_6$-halocycloalkylthio, $C_3$-$C_6$-cycloalkyl-$C_1$-$C_6$-alkylthio, $C_3$-$C_6$-halocycloalkyl-$C_1$-$C_6$-alkylthio, $C_3$-$C_6$-cycloalkyl-$C_1$-$C_6$-haloalkylthio, $C_3$-$C_6$-halocycloalkyl-$C_1$-$C_6$-haloalkylthio, heterocyclylthio, phenylthio, phenyl-$C_1$-$C_6$-alkylthio, heterocyclyl-$C_1$-$C_6$-alkylthio, $C_1$-$C_6$-alkylsulfonyl, $C_1$-$C_6$-haloalkylsulfonyl, $C_3$-$C_6$-cycloalkylsulfonyl, $C_3$-$C_6$-halocycloalkylsulfonyl, heterocyclylsulfonyl, phenylsulfonyl, phenyl-$C_1$-$C_6$-alkylsulfonyl, heterocyclyl-$C_1$-$C_6$-alkylsulfonyl, $C_1$-$C_6$-alkylsulfinyl, $C_1$-$C_6$-haloalkylsulfinyl, $C_3$-$C_6$-cycloalkylsulfinyl, $C_3$-$C_6$-halocycloalkylsulfinyl, heterocyclylsulfinyl, phenylsulfinyl, phenyl-$C_1$-$C_6$-alkylsulfinyl, heterocyclyl-$C_1$-$C_6$-alkylsulfinyl, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl) amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl) amino, [N—($C_1$-$C_6$-alkyl), N-(phenyl-$C_1$-$C_6$-alkyl)] amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)] amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II.

(II)

wherein

Q is hydrogen or $C_1$-$C_6$-alkyl;

Y is a direct bond or $C_1$-$C_6$-alkanediyl;

$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

X $OR^4$, $SR^5$; $NR^6R^7$;

$R^4$, $R^5$ hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_2$-$C_6$-alkenyloxy-$C_1$-$C_6$-alkyl, $C_2$-$C_6$-haloalkenyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkyl-aminocarbonyl-$C_1$-$C_6$-alkyl, N,N-di-($C_1$-$C_6$-alkyl)-aminocarbonyl-$C_1$-$C_6$-alkyl, [N—($C_3$-$C_6$-cycloalkyl-$C_1$-$C_6$-alkyl), N—($C_1$-$C_6$-alkyl)]-aminocarbonyl-$C_1$-$C_6$-alkyl, $C_1$-$C_6$-alkoxy-aminocarbonyl-$C_1$-$C_6$-alkyl, $C_2$-$C_6$-alkenyl, $C_2$-$C_6$-haloalkenyl, $C_2$-$C_6$-alkynyl-$C_2$-$C_6$-alkenyl, $C_3$-$C_6$-alkynyl, $C_3$-$C_6$-haloalkynyl, heterocyclyl, phenyl, heterocyclylcarbonyl, phenylcarbonyl, heterocyclylcarbonyl-$C_1$-$C_6$-alkyl, phenylcarbonyl-$C_1$-$C_6$-alkyl, heterocyclyl-$C_1$-$C_6$-alkyl, phenyl-$C_1$-$C_6$-alkyl; wherein the phenyl and heterocyclyl moieties of $R^4$ and $R^5$ can be unsubstituted or substituted with one or more radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;

$R^6$, $R^7$ hydrogen, $C_1$-$C_6$-alkyl, $C_1$-$C_6$-haloalkyl;

and their agriculturally useful salts.

In addition, subject matter of the present invention is the use of isoxazolo[5,4-b]pyridines of formula I as herbicides, i.e. their use for controlling harmful plants.

The present invention also provides compositions comprising at least one isoxazolo[5,4-b]pyridine of formula I and auxiliaries customary for formulating crop protection agents.

The present invention furthermore provides a method for controlling unwanted vegetation, where a herbicidal effective amount of at least one isoxazolo[5,4-b]pyridine of formula I is allowed to act on plants, their seeds and/or their habitat. Application can be done before, during and/or after, preferably during and/or after, the emergence of the undesirable plants.

Moreover, the invention relates to processes for preparing isoxazolo[5,4-b]pyridines of formula I.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation", "weeds" and "harmful plants" are synonyms.

If the isoxazolo[5,4-b]pyridines of formula I as described herein are capable of forming geometrical isomers, for example E/Z isomers, it is possible to use both, the pure isomers and mixtures thereof, in the compositions according to the invention.

If the isoxazolo[5,4-b]pyridines of formula I as described herein have one or more centers of chirality and, as a consequence, are present as enantiomers or diastereomers, it is possible to use both, the pure enantiomers and diastereomers and their mixtures, in the compositions according to the invention.

The terms used for organic groups in the definition of the variables are, for example the expression "alkyl", collective terms which represent the individual members of these groups of organic units.

The prefix $C_x$-$C_y$ denotes the number of possible carbon atoms in the particular case.

halogen: fluorine, chlorine, bromine or iodine, especially fluorine, chlorine or bromine;

alkyl and the alkyl moieties of composite groups such as alkoxy, alkylamino, alkylthio, alkoxycarbonyl: saturated straight-chain or branched hydrocarbon radicals having 1 to 10 carbon atoms, preferably $C_1$-$C_6$-alkyl or $C_1$-$C_4$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl, 2-ethylhexyl and positional isomers thereof; nonyl, decyl and positional isomers thereof;

haloalkyl: straight-chain or branched alkyl groups having 1 to 10 carbon atoms (as mentioned above), preferably $C_1$-$C_6$-haloalkyl or $C_1$-$C_4$-haloalkyl, where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_3$)-haloalkyl, more preferably ($C_1$-$C_2$)-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl;

alkenyl and also the alkenyl moieties in composite groups, such as alkenyloxy: unsaturated straight-chain or branched hydrocarbon radicals having 2 to 10 carbon atoms and one double bond in any position. According to the invention, it may be preferred to use small alkenyl groups, such as ($C_2$-$C_6$)-alkenyl; on the other hand, it may also be preferred to employ larger alkenyl groups, such as ($C_5$-$C_8$)-alkenyl. Examples of $C_2$-$C_6$-alkenyl groups are: ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl and the alkynyl moieties in composite groups: straight-chain or branched hydrocarbon groups having 2 to 10 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl and also the cycloalkyl moieties in composite groups: mono- or bicyclic saturated hydrocarbon groups having 3 to 10, in particular 3 to 6, carbon ring members. Examples for $C_3$-$C_6$-cycloalkyl are: cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl;

cycloalkyloxy: a cycloalkyl group as defined above, which is attached via an oxygen, Examples are: cyclopropyloxy, cyclobutyloxy, cyclopentyloxy, cyclohexyloxy, cycloheptyloxy or cyclooctyloxy.

halocycloalkyl and the halocycloalkyl moieties in composite groups: monocyclic saturated hydrocarbon groups having 3 to 10 carbon ring members (as mentioned above) in which some or all of the hydrogen atoms may be replaced by halogen atoms as mentioned above, in particular fluorine, chlorine and bromine;

cycloalkenyl: monocyclic monounsaturated hydrocarbon groups having 3 to 10, 3 to 8, 3 to 6, preferably 5 to 6, carbon ring members, such as cyclopenten-1-yl, cyclopenten-3-yl, cyclohexen-1-yl, cyclohexen-3-yl, cyclohexen-4-yl and the like;

alkoxy: an alkyl group as defined above, which is attached via an oxygen, preferably having 1 to 10, more preferably 1 to 6 or 1 to 4 carbon atoms. Examples are: methoxy, ethoxy, n-propoxy, 1-methylethoxy, butoxy, 1-methylpropoxy, 2-methylpropoxy or 1,1-dimethylethoxy, and also for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

haloalkoxy: alkoxy as defined above, where some or all of the hydrogen atoms in these groups are replaced by halogen atoms as described above under haloalkyl, in particular by fluorine, chlorine or bromine. Examples are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy; and also 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

aryl: 6 to 10-membered, aromatic carbocycle with 6, 7, 8, 9 or 10 carbon atoms. Examples of preferred aryl are phenyl or naphthyl;

heterocycle: 5-, 6-, 7-, 8-, 9- or 10-membered saturated, partially unsaturated or aromatic monocyclic ring or bicyclic ring system, which contains 1, 2, 3 or 4 heteroatoms from the group consisting of O, N and S as ring members, and may furthermore contain one or two CO, SO, $SO_2$ groups as ring members, where the heterocycle in question may be attached via a carbon atom or, if present, via a nitrogen atom. In particular:

a three, five- or six-membered saturated or partially unsaturated heterocycle which comprises one, two, three or four heteroatoms from the group consisting of O, N and S as ring members: for example monocyclic saturated or partially unsaturated heterocycles which, in addition to carbon ring members, comprise one, two or three nitrogen atoms and/or one oxygen or sulfur atom or one or two oxygen and/or sulfur atoms, for example aziridine, oxirane, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding -ylidene radicals;

a seven-membered saturated or partially unsaturated heterocycle which comprises one, two, three or four heteroatoms from the group consisting of O, N and S as ring members: for example mono- and bicyclic heterocycles having 7 ring members which, in addition to carbon ring members, comprise one, two or three nitrogen atoms and/or one oxygen or sulfur atom or one or two oxygen and/or sulfur atoms, for example tetra- and hexahydroazepinyl, such as 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, hexahydroazepin-1-, -2-, -3- or -4-yl, tetra- and hexahydrooxepinyl such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, hexahydroazepin-1-, -2-, -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding ylidene radicals;

a five- or six-membered aromatic heterocycle (=heteroaromatic radical) which contains one, two, three or four heteroatoms from the group consisting of oxygen, nitrogen and sulfur, for example 5-membered heteroaryl which is attached via carbon and contains one to three nitrogen atoms or one or two nitrogen atoms and one sulfur or oxygen atom as ring members, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 5-membered heteroaryl which is attached via nitrogen and contains one to three nitrogen atoms as ring members, such as pyrrol-1-yl, pyrazol-1-yl, imidazol-1-yl, 1,2,3-triazol-1-yl and 1,2,4-triazol-1-yl; 6-membered heteroaryl, which contains one, two or three nitrogen atoms as ring members, such as pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

The isoxazolo[5,4-b]pyridines of formula I may also be present in the form of the N-oxides and/or their agriculturally useful salts, the nature of the salt being, as a rule, immaterial. In general, suitable salts are the salts of those cations or the acid addition salts of those acids whose cations, or anions, respectively, do not adversely affect the herbicidal activity of the isoxazolo[5,4-b]pyridines of formula I.

Suitable cations are, in particular, ions of the alkali metals, preferably lithium, sodium or potassium, of the alkaline-earth metals, preferably calcium or magnesium, and of the transition metals, preferably manganese, copper, zinc or iron. Likewise, it is possible to use ammonium as the cation, where, if desired, one to four hydrogen atoms may be replaced by $C_1$-$C_4$-alkyl, hydroxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Others which are suitable are phosphonium ions, sulfonium ions, preferably tri($C_1$-$C_4$-alkyl)sulfonium or sulfoxonium ions, preferably tri($C_1$-$C_4$-alkyl)sulfoxonium. Anions of useful acid addition salts are, mainly, chloride, bromide, fluoride, hydrogensulfate, sulfate, dihydrogenphosphate, hydrogenphosphate, nitrate, hydrogencarbonate, carbonate, hexafluorosilicate, hexafluorophosphate, benzoate and the anions of $C_1$-$C_4$-alkanoic acids, preferably formate, acetate, propionate, butyrate or trifluoracetate.

In general, isoxazolo[5,4-b]pyridines of formula I are suitable as herbicides.

Isoxazolo[5,4-b]pyridine compounds of formula I.a (formula I.a corresponds to formula I, wherein $R^1$ is hydrogen and $R^2$ is cyclopropyl)

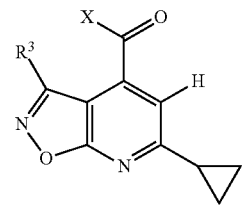

I.a or their agriculturally useful salts are particularly useful as herbicides.

Preferred embodiments of the isoxazolo[5,4-b]pyridine compounds of formula I.a are compounds 1.a.1 to 1.a.40 according to table 1, wherein each line of table 1 represents one compound of formula I:

TABLE 1

Isoxazolo[5,4-b]pyridine compounds 1.a.1 to 1.a.40

| No. | $R^3$ | X |
|---|---|---|
| I.a.1. | cyclopropyl-NH- | —OH |
| I.a.2. | cyclopropyl-NH- | —OCH$_2$OCH$_3$ |

TABLE 1-continued

Isoxazolo[5,4-b]pyridine compounds 1.a.1 to 1.a.40

| No. | R³ | X |
|---|---|---|
| I.a.3. | cyclopropyl-NH- | —NH₂ |
| I.a.4. | cyclopropyl-NH- | —SCH₃ |
| I.a.5. | 2,2-difluorocyclopropyl-NH- | —OH |
| I.a.6. | 2,2-difluorocyclopropyl-NH- | —OCH₂OCH₃ |
| I.a.7. | 2,2-difluorocyclopropyl-NH- | —NH₂ |
| I.a.8. | 2,2-difluorocyclopropyl-NH- | —SCH₃ |
| I.a.9. | 4-fluorocyclohexyl-NH- | —OH |
| I.a.10. | 4-fluorocyclohexyl-NH- | —OCH₂OCH₃ |
| I.a.11. | 4-fluorocyclohexyl-NH- | —NH₂ |
| I.a.12. | 4-fluorocyclohexyl-NH- | —SCH₃ |
| I.a.13. | cyclopropylmethyl-NH- | —OH |
| I.a.14. | cyclopropylmethyl-NH- | —OCH₂OCH₃ |
| I.a.15. | cyclopropylmethyl-NH- | —NH₂ |
| I.a.16. | cyclopropylmethyl-NH- | —SCH₃ |
| I.a.17. | oxetan-3-yloxy- | —OH |
| I.a.18. | oxetan-3-yloxy- | —OCH₂OCH₃ |
| I.a.19. | oxetan-3-yloxy- | —NH₂ |
| I.a.20. | oxetan-3-yloxy- | —SCH₃ |
| I.a.21. | tetrahydropyran-4-yloxy- | —OH |
| I.a.22. | tetrahydropyran-4-yloxy- | —OCH₂OCH₃ |
| I.a.23. | tetrahydropyran-4-yloxy- | —NH₂ |
| I.a.24. | tetrahydropyran-4-yloxy- | —SCH₃ |
| I.a.25. | cyclopentyloxy- | —OH |

TABLE 1-continued

Isoxazolo[5,4-b]pyridine compounds 1.a.1 to 1.a.40

| No. | R³ | X |
|---|---|---|
| I.a.26. | cyclopentyl-O- | —OCH₂OCH₃ |
| I.a.27. | cyclopentyl-O- | —NH₂ |
| I.a.28. | cyclopentyl-O- | —SCH₃ |
| I.a.29. | 4,4-difluorocyclohexyl-O- | —OH |
| I.a.30. | 4,4-difluorocyclohexyl-O- | —OCH₂OCH₃ |
| I.a.31. | 4,4-difluorocyclohexyl-O- | —NH₂ |
| I.a.32. | 4,4-difluorocyclohexyl-O- | —SCH₃ |
| I.a.33. | cyclohexyl-O- | —OH |
| I.a.34. | cyclohexyl-O- | —OCH₂OCH₃ |
| I.a.35. | cyclohexyl-O- | —NH₂ |
| I.a.36. | cyclohexyl-O- | —SCH₃ |
| I.a.37. | PhNH- | —OH |
| I.a.38. | PhNH- | —OCH₂OCH₃ |
| I.a.39. | PhNH- | —NH₂ |
| I.a.40. | PhNH- | —SCH₃ |

In addition, the following isoxazolo[5,4-b]pyridine compounds of formula I are particularly useful as herbicides:

Isoxazolo[5,4-b]pyridine compounds of formula I.b (formula I.b corresponds to formula I, wherein $R^1$ is hydrogen and $R^2$ is 1-fluorocyclopropyl)

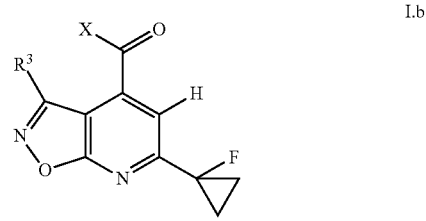

I.b or their agriculturally useful salts are particularly useful as herbicides.

Preferred embodiments of the isoxazolo[5,4-b]pyridine compounds of formula I.b are compounds 1.b.1 to 1.b.40, which differ from the isoxazolo[5,4-b]pyridine compounds I.a.1 to I.a.40 according to table 1 only regarding the variable $R^2$, which is 1-fluorocyclopropyl).

According to a preferred embodiment of the invention preference is also given to those isoxazolo[5,4-b]pyridine compounds of formula I, wherein $R^1$ is hydrogen, halogen, $C_1$-$C_6$-alkyl, $C_1$-$C_6$-haloalkyl;

Particularly preferred are those isoxazolo[5,4-b]pyridine compounds of formula I, wherein $R^1$ is hydrogen.

According to another preferred embodiment of the invention, preference is also given to those isoxazolo[5,4-b]pyridine compounds of formula I, wherein $R^2$ is $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl, $C_2$-$C_6$-alkynyl;

Very particularly preferred are those isoxazolo[5,4-b]pyridine compounds of formula I, wherein $R^2$ is $C_3$-$C_6$-cycloalkyl or $C_3$-$C_6$-halocycloalkyl; Most particularly preferred are those isoxazolo[5,4-b]pyridine compounds of formula I, wherein is $R^2$ is cyclopropyl or 1-fluorocyclopropyl.

According to another preferred embodiment of the invention, preference is also given to those isoxazolo[5,4-b]pyridine compounds of formula I, wherein
$R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, $C_3$-$C_6$-cycloalkylthio, $C_3$-$C_6$-halocycloalkylthio, $C_3$-$C_6$-cycloalkyl-$C_1$-$C_6$-alkylthio, $C_3$-$C_6$-halocycloalkyl-$C_1$-$C_6$-alkylthio, $C_3$-$C_6$-cycloalkyl-$C_1$-$C_6$-haloalkylthio, $C_3$-$C_6$-halocycloalkyl-$C_1$-$C_6$-haloalkylthio, heterocyclylthio, phenylthio, phenyl-$C_1$-$C_6$-alkylthio, heterocyclyl-$C_1$-$C_6$-alkylthio, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II, wherein
Q is hydrogen or $C_1$-$C_6$-alkyl;
Y is a direct bond or $C_1$-$C_6$-alkanediyl;
$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

According to another preferred embodiment of the invention, preference is also given to those isoxazolo[5,4-b]pyridine compounds of formula I, wherein
$R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II.

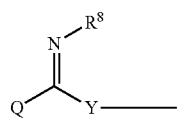

(II)

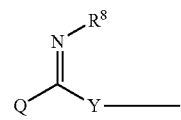

(II)

wherein
Q is hydrogen or $C_1$-$C_6$-alkyl;
Y is a direct bond or $C_1$-$C_6$-alkanediyl;
$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

According to another preferred embodiment of the invention, preference is also given to those isoxazolo[5,4-b]pyridine compounds of formula I, wherein
$R^3$ is $C_1$-$C_6$-alkyl-carbonyloxy-$C_1$-$C_6$-alkyl, $C_1$-$C_6$-alkyl-carbonyl-$C_1$-$C_6$-alkyl, formyl, formyl-$C_1$-$C_6$-alkyl, $C_3$-$C_6$-cycloalkyloxy, $C_3$-$C_6$-halocycloalkyloxy, $C_3$-$C_6$-cycloalkyl-$C_1$-$C_6$-alkoxy, $C_3$-$C_6$-alkenyloxy, $C_3$-$C_6$-alkynyloxy, $C_1$-$C_6$-alkoxy-$C_1$-$C_6$-alkoxy, phenyl-$C_1$-$C_6$-alkoxy, phenoxy, heterocyclyloxy, phenylcarbonyloxy, $C_3$-$C_6$-cycloalkylthio, phenylthio, phenyl-$C_1$-$C_6$-alkylthio, phenylamino, N—($C_3$-$C_6$-cycloalkyl)amino, N—[($C_3$-$C_6$-cycloalkyl)-($C_1$-$C_6$-alkyl)]amino, wherein the phenyl moieties of $R^3$ can be unsubstituted or substituted with $C_1$-$C_6$-haloalkyl, the moiety of formula II, (II)

wherein
Q is hydrogen or $C_1$-$C_6$-alkyl;
Y is a direct bond or $C_1$-$C_6$-alkanediyl;
$R^8$ is amino, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

According to another preferred embodiment of the invention, preference is also given to those isoxazolo[5,4-b]pyridine compounds of formula I, wherein
$R^3$ is $C_1$-$C_6$-alkyl-carbonyloxy-$C_1$-$C_6$-alkyl, $C_1$-$C_6$-alkyl-carbonyl-$C_1$-$C_6$-alkyl, formyl, formyl-$C_1$-$C_6$-alkyl, $C_3$-$C_6$-cycloalkyloxy, $C_3$-$C_6$-halocycloalkyloxy, $C_3$-$C_6$-cycloalkyl-$C_1$-$C_6$-alkoxy, $C_3$-$C_6$-alkenyloxy, $C_3$-$C_6$-alkynyloxy, $C_1$-$C_6$-alkoxy-$C_1$-$C_6$-alkoxy, phenyl-$C_1$-$C_6$-alkoxy, phenoxy, heterocyclyloxy, phenylcarbonyloxy, phenyl-amino, N—($C_3$-$C_6$-cycloalkyl)amino, N—[($C_3$-$C_6$-cycloalkyl)-($C_1$-$C_6$-alkyl)]amino, the moiety of formula II, (II)

wherein
Q is hydrogen or $C_1$-$C_6$-alkyl;
Y is a direct bond or $C_1$-$C_6$-alkanediyl;
$R^8$ is amino, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

According to another preferred embodiment of the invention, preference is also given to those isoxazolo[5,4-b]pyridine compounds of formula I, wherein
$R^3$ is $C_1$-$C_6$-alkyl-carbonyloxy-$C_1$-$C_6$-alkyl, $C_1$-$C_6$-alkyl-carbonyl-$C_1$-$C_6$-alkyl, formyl, formyl-$C_1$-$C_6$-alkyl, $C_3$-$C_6$-cycloalkyloxy, $C_3$-$C_6$-alkenyloxy, $C_3$-$C_6$-alkynyloxy, $C_1$-$C_6$-alkoxy-$C_1$-$C_6$-alkoxy, phenyl-$C_1$-$C_6$-alkoxy, phenoxy, phenylcarbonyloxy, phenyl-amino, N—($C_3$-$C_6$-cycloalkyl)amino, N—[($C_3$-$C_6$-cycloalkyl)-($C_1$-$C_6$-alkyl)]amino, the moiety of formula II, (II)

wherein
Q is hydrogen or $C_1$-$C_6$-alkyl;
Y is a direct bond or $C_1$-$C_6$-alkanediyl;
$R^8$ is hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

According to another preferred embodiment of the invention, preference is also given to those isoxazolo[5,4-b]pyridine compounds of formula I, wherein
$R^3$ is $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy.

Particularly preferred are those isoxazolo[5,4-b]pyridine compounds of formula I, wherein $R^3$ is $C_3$-$C_6$-cycloalkyloxy, $C_3$-$C_6$-halocycloalkyloxy, phenylamino or N—($C_3$-$C_6$-cycloalkyl)amino;

Very particularly preferred are those isoxazolo[5,4-b]pyridine compounds of formula I, wherein $R^3$ is $C_3$-$C_6$-cycloalkyloxy or $C_3$-$C_6$-halocycloalkyloxy.

According to another preferred embodiment of the invention, preference is also given to those isoxazolo[5,4-b]pyridine compounds of formula I, wherein
X is $OR^4$.

According to another preferred embodiment of the invention, preference is also given to those isoxazolo[5,4-b]pyridine compounds of formula I, wherein,
$R^4$ is hydrogen, $C_1$-$C_6$-alkyl, $C_1$-$C_6$-haloalkyl, $C_1$-$C_6$-cyanoalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_3$-$C_6$-alkynyl.

Particularly preferred are those isoxazolo[5,4-b]pyridine compounds of formula I, wherein $R^4$ is hydrogen, methyl, ethyl, n-propyl, i-propyl, n-butyl, 1-methylpropyl, 2-methylpropyl, tert-butyl; Most particularly preferred are those isoxazolo[5,4-b]pyridine compounds of formula I, wherein is $R^4$ is hydrogen;

According to another preferred embodiment of the invention, preference is also given to those isoxazolo[5,4-b]pyridine compounds of formula I, wherein
X is $SR^5$.

According to another preferred embodiment of the invention, preference is also given to those isoxazolo[5,4-b]pyridine compounds of formula I, wherein, $R^5$ is hydrogen, $C_1$-$C_6$-alkyl, $C_1$-$C_6$-haloalkyl, phenyl-$C_1$-$C_6$-alkyl, $C_2$-$C_6$-alkenyl, $C_2$-$C_6$-haloalkenyl, $C_3$-$C_6$-alkynyl;

Particularly preferred are those isoxazolo[5,4-b]pyridine compounds of formula I, wherein $R^5$ is $C_1$-$C_6$-alkyl, $C_1$-$C_6$-haloalkyl, phenyl-$C_1$-$C_6$-alkyl. Most particularly preferred are those isoxazolo[5,4-b]pyridine compounds of formula I, wherein $R^5$ is $C_1$-$C_6$-alkyl or phenyl-$C_1$-$C_6$-alkyl.

Particularly useful as herbicides are those isoxazolo[5,4-b]pyridine compounds of formula I, wherein $R^1$ is hydrogen;

$R^2$ is $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl, $C_2$-$C_6$-alkynyl;

$R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, $C_3$-$C_6$-cycloalkylthio, $C_3$-$C_6$-halocycloalkylthio, $C_3$-$C_6$-cycloalkyl-$C_1$-$C_6$-alkylthio, $C_3$-$C_6$-halocycloalkyl-$C_1$-$C_6$-alkylthio, $C_3$-$C_6$-cycloalkyl-$C_1$-$C_6$-haloalkylthio, $C_3$-$C_6$-halocycloalkyl-$C_1$-$C_6$-haloalkylthio, heterocyclylthio, phenylthio, phenyl-$C_1$-$C_6$-alkylthio, heterocyclyl-$C_1$-$C_6$-alkylthio, $C_1$-$C_6$-alkylsulfonyl, $C_1$-$C_6$-haloalkylsulfonyl, $C_3$-$C_6$-cycloalkylsulfonyl, $C_3$-$C_6$-halocycloalkylsulfonyl, heterocyclylsulfonyl, phenylsulfonyl, phenyl-$C_1$-$C_6$-alkylsulfonyl, heterocyclyl-$C_1$-$C_6$-alkylsulfonyl, $C_1$-$C_6$-alkylsulfinyl, $C_1$-$C_6$-haloalkylsulfinyl, $C_3$-$C_6$-cycloalkylsulfinyl, $C_3$-$C_6$-halocycloalkylsulfinyl, heterocyclylsulfinyl, phenylsulfinyl, phenyl-$C_1$-$C_6$-alkylsulfinyl, heterocyclyl-$C_1$-$C_6$-alkylsulfinyl, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II,

(II)

wherein

Q is hydrogen or $C_1$-$C_6$-alkyl;

Y is a direct bond or $C_1$-$C_6$-alkanediyl;

$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

X is $OR^4$;

$R^4$ is hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_2$-$C_6$-alkenyloxy-$C_1$-$C_6$-alkyl, $C_2$-$C_6$-haloalkenyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkyl-aminocarbonyl-$C_1$-$C_6$-alkyl, N,N-di-($C_1$-$C_6$-alkyl)-aminocarbonyl-$C_1$-$C_6$-alkyl, [N—($C_3$-$C_6$-cycloalkyl-$C_1$-$C_6$-alkyl), N—($C_1$-$C_6$-alkyl)]aminocarbonyl-$C_1$-$C_6$-alkyl, $C_1$-$C_6$-alkoxy-aminocarbonyl-$C_1$-$C_6$-alkyl, $C_2$-$C_6$-alkenyl, $C_2$-$C_6$-haloalkenyl, $C_2$-$C_6$-alkynyl-$C_2$-$C_6$-alkenyl, $C_3$-$C_6$-alkynyl, $C_3$-$C_6$-haloalkynyl, heterocyclyl, phenyl, heterocyclylcarbonyl, phenylcarbonyl, heterocyclylcarbonyl-$C_1$-$C_6$-alkyl, phenylcarbonyl-$C_1$-$C_6$-alkyl, heterocyclyl-$C_1$-$C_6$-alkyl, phenyl-$C_1$-$C_6$-alkyl; wherein the phenyl and heterocyclyl moieties of $R^4$ and $R^5$ can be unsubstituted or substituted with one or more radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;

and their agriculturally useful salts;

Particularly useful as herbicides are those isoxazolo[5,4-b]pyridine compounds of formula I, wherein $R^1$ is hydrogen;

$R^2$ is $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl, $C_2$-$C_6$-alkynyl; $R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II,

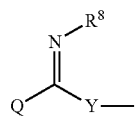

(II)

wherein
Q is hydrogen or $C_1$-$C_6$-alkyl;
Y is a direct bond or $C_1$-$C_6$-alkanediyl;
$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];
X is $OR^4$;
$R^4$ is hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_2$-$C_6$-alkenyloxy-$C_1$-$C_6$-alkyl, $C_2$-$C_6$-haloalkenyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkyl-aminocarbonyl-$C_1$-$C_6$-alkyl, N,N-di-($C_1$-$C_6$-alkyl)-aminocarbonyl-$C_1$-$C_6$-alkyl, [N—($C_3$-$C_6$-cycloalkyl-$C_1$-$C_6$-alkyl), N—($C_1$-$C_6$-alkyl)]aminocarbonyl-$C_1$-$C_6$-alkyl, $C_1$-$C_6$-alkoxy-aminocarbonyl-$C_1$-$C_6$-alkyl, $C_2$-$C_6$-alkenyl, $C_2$-$C_6$-haloalkenyl, $C_2$-$C_6$-alkynyl-$C_2$-$C_6$-alkenyl, $C_3$-$C_6$-alkynyl, $C_3$-$C_6$-haloalkynyl, heterocyclyl, phenyl, heterocyclylcarbonyl, phenylcarbonyl, heterocyclylcarbonyl-$C_1$-$C_6$-alkyl, phenylcarbonyl-$C_1$-$C_6$-alkyl, heterocyclyl-$C_1$-$C_6$-alkyl, phenyl-$C_1$-$C_6$-alkyl; wherein the phenyl and heterocyclyl moieties of $R^4$ and $R^5$ can be unsubstituted or substituted with one or more radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;
and their agriculturally useful salts;
Particularly useful as herbicides are those isoxazolo[5,4-b]pyridine compounds of formula I, wherein $R^1$ is hydrogen;
$R^2$ is $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl, $C_2$-$C_6$-alkynyl;
$R^3$ is $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy;
X is $OR^4$;
$R^4$ is hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_2$-$C_6$-alkenyloxy-$C_1$-$C_6$-alkyl, $C_2$-$C_6$-haloalkenyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkyl-aminocarbonyl-$C_1$-$C_6$-alkyl, N,N-di-($C_1$-$C_6$-alkyl)-aminocarbonyl-$C_1$-$C_6$-alkyl, [N—($C_3$-$C_6$-cycloalkyl-$C_1$-$C_6$-alkyl), N—($C_1$-$C_6$-alkyl)]aminocarbonyl-$C_1$-$C_6$-alkyl, $C_1$-$C_6$-alkoxy-aminocarbonyl-$C_1$-$C_6$-alkyl, $C_2$-$C_6$-alkenyl, $C_2$-$C_6$-haloalkenyl, $C_2$-$C_6$-alkynyl-$C_2$-$C_6$-alkenyl, $C_3$-$C_6$-alkynyl, $C_3$-$C_6$-haloalkynyl, heterocyclyl, phenyl, heterocyclylcarbonyl, phenylcarbonyl, heterocyclylcarbonyl-$C_1$-$C_6$-alkyl, phenylcarbonyl-$C_1$-$C_6$-alkyl, heterocyclyl-$C_1$-$C_6$-alkyl, phenyl-$C_1$-$C_6$-alkyl; wherein the phenyl and heterocyclyl moieties of $R^4$ and $R^5$ can be unsubstituted or substituted with one or more radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;
and their agriculturally useful salts;

Particularly useful as herbicides are those isoxazolo[5,4-b]pyridine compounds of formula I, wherein $R^1$ is hydrogen;

$R^2$ is hydrogen, $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl, $C_2$-$C_6$-alkynyl;

$R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, $C_3$-$C_6$-cycloalkylthio, $C_3$-$C_6$-halocycloalkylthio, $C_3$-$C_6$-cycloalkyl-$C_1$-$C_6$-alkylthio, $C_3$-$C_6$-halocycloalkyl-$C_1$-$C_6$-alkylthio, $C_3$-$C_6$-cycloalkyl-$C_1$-$C_6$-haloalkylthio, $C_3$-$C_6$-halocycloalkyl-$C_1$-$C_6$-haloalkylthio, heterocyclylthio, phenylthio, phenyl-$C_1$-$C_6$-alkylthio, heterocyclyl-$C_1$-$C_6$-alkylthio, $C_1$-$C_6$-alkylsulfonyl, $C_1$-$C_6$-haloalkylsulfonyl, $C_3$-$C_6$-cycloalkylsulfonyl, $C_3$-$C_6$-halocycloalkylsulfonyl, heterocyclylsulfonyl, phenylsulfonyl, phenyl-$C_1$-$C_6$-alkylsulfonyl, heterocyclyl-$C_1$-$C_6$-alkylsulfonyl, $C_1$-$C_6$-alkylsulfinyl, $C_1$-$C_6$-haloalkylsulfinyl, $C_3$-$C_6$-cycloalkylsulfinyl, $C_3$-$C_6$-halocycloalkylsulfinyl, heterocyclylsulfinyl, phenylsulfinyl, phenyl-$C_1$-$C_6$-alkylsulfinyl, heterocyclyl-$C_1$-$C_6$-alkylsulfinyl, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II,

wherein

Q is hydrogen or $C_1$-$C_6$-alkyl;

Y is a direct bond or $C_1$-$C_6$-alkanediyl;

$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];

X is $SR^5$;

$R^5$ is hydrogen, $C_1$-$C_6$-alkyl, $C_1$-$C_6$-haloalkyl, phenyl-$C_1$-$C_6$-alkyl; is most preferably $C_1$-$C_6$-alkyl, phenyl-$C_1$-$C_6$-alkyl;

and their agriculturally useful salts;

More particularly useful as herbicides are those isoxazolo[5,4-b]pyridine compounds of formula I, wherein $R^1$ is hydrogen;

$R^2$ is $C_3$-$C_6$-cycloalkyl, $C_3$-$C_6$-halocycloalkyl; most preferably cyclopropyl or 1-fluorocyclopropyl;

$R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, $C_3$-$C_6$-cycloalkylthio, $C_3$-$C_6$-halocycloalkylthio, $C_3$-$C_6$-cycloalkyl-$C_1$-$C_6$-alkylthio, $C_3$-$C_6$-halocycloalkyl-$C_1$-$C_6$-alkylthio, $C_3$-$C_6$-cycloalkyl-$C_1$-$C_6$-haloalkylthio, $C_3$-$C_6$-halocycloalkyl-$C_1$-$C_6$-haloalkylthio, heterocyclylthio, phenylthio, phenyl-$C_1$-$C_6$-alkylthio, heterocyclyl-$C_1$-$C_6$-alkylthio, $C_1$-$C_6$-alkylsulfonyl, $C_1$-$C_6$-haloalkylsulfonyl, $C_3$-$C_6$-cycloalkylsulfonyl, $C_3$-$C_6$-halocycloalkylsulfonyl, heterocyclylsulfonyl, phenylsulfonyl, phenyl-$C_1$-$C_6$-alkylsulfonyl, heterocyclyl-$C_1$-$C_6$-alkylsulfonyl, $C_1$-$C_6$-alkylsulfinyl, $C_1$-$C_6$-haloalkylsulfinyl, $C_3$-$C_6$-cycloalkylsulfinyl, $C_3$-$C_6$-halocycloalkylsulfinyl, heterocyclylsulfinyl, phenylsulfinyl, phenyl-$C_1$-$C_6$-alkylsulfinyl, heterocyclyl-$C_1$-$C_6$-alkylsulfinyl, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$- alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II,

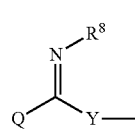

(II)

wherein
Q is hydrogen or $C_1$-$C_6$-alkyl;
Y is a direct bond or $C_1$-$C_6$-alkanediyl;
$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];
X is $OR^4$;
$R^4$ is hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_2$-$C_6$-alkenyloxy-$C_1$-$C_6$-alkyl, $C_2$-$C_6$-haloalkenyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkyl-aminocarbonyl-$C_1$-$C_6$-alkyl, N,N-di-($C_1$-$C_6$-alkyl)-aminocarbonyl-$C_1$-$C_6$-alkyl, [N—($C_3$-$C_6$-cycloalkyl-$C_1$-$C_6$-alkyl), N—($C_1$-$C_6$-alkyl)]aminocarbonyl-$C_1$-$C_6$-alkyl, $C_1$-$C_6$-alkoxy-aminocarbonyl-$C_1$-$C_6$-alkyl, $C_2$-$C_6$-alkenyl, $C_2$-$C_6$-haloalkenyl, $C_2$-$C_6$-alkynyl-$C_2$-$C_6$-alkenyl, $C_3$-$C_6$-alkynyl, $C_3$-$C_6$-haloalkynyl, heterocyclyl, phenyl, heterocyclylcarbonyl, phenylcarbonyl, heterocyclylcarbonyl-$C_1$-$C_6$-alkyl, phenylcarbonyl-$C_1$-$C_6$-alkyl, heterocyclyl-$C_1$-$C_6$-alkyl, phenyl-$C_1$-$C_6$-alkyl; wherein the phenyl and heterocyclyl moieties of $R^4$ and $R^5$ can be unsubstituted or substituted with one or more radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;
and their agriculturally useful salts;
More particularly useful as herbicides are those isoxazolo[5,4-b]pyridine compounds of formula I, wherein
$R^1$ is hydrogen;
$R^2$ is $C_3$-$C_6$-cycloalkyl, $C_3$-$C_6$-halocycloalkyl; most preferably cyclopropyl or 1-fluorocyclopropyl;
$R^3$ is $C_3$-$C_6$-cycloalkyloxy-$C_1$-$C_6$-alkyl, $C_3$-$C_6$-halocycloalkyloxy-$C_1$-$C_6$-alkyl, phenoxy-$C_1$-$C_6$-alkyl, heterocyclyloxy-$C_1$-$C_6$-alkyl, phenyl-$C_1$-$C_6$-alkoxy-$C_1$-$C_6$-alkyl, $C_1$-$C_6$-alkyl-carbonyloxy-$C_1$-$C_6$-alkyl, amino-$C_1$-$C_6$-alkyl, ($C_1$-$C_6$-alkyl)amino-$C_1$-$C_6$-alkyl, N,N-di-($C_1$-$C_6$-alkyl)amino-$C_1$-$C_6$-alkyl, ($C_3$-$C_6$-cycloalkyl)amino-$C_1$-$C_6$-alkyl, N,N-di-($C_3$-$C_6$-cycloalkyl)amino-$C_1$-$C_6$-alkyl, [N—($C_1$-$C_6$-alkyl), N—($C_3$-$C_6$-cycloalkyl)]amino-$C_1$-$C_6$-alkyl, $C_1$-$C_6$-alkyl-carbonyl-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, $C_1$-$C_6$-alkoxy-$C_1$-$C_6$-alkoxy-$C_1$-$C_6$-alkyl, formyl, formyl-$C_1$-$C_6$-alkyl, $C_1$-$C_6$-alkyl-carbonyl, $C_3$-$C_6$-cycloalkyloxy, $C_3$-$C_6$-halocycloalkyloxy, $C_1$-$C_6$-alkyl-$C_3$-$C_6$-cycloalkyloxy, $C_1$-$C_6$-alkyl-$C_3$-$C_6$-halocycloalkyloxy, $C_1$-$C_6$-haloalkyl-$C_3$-$C_6$-cycloalkyloxy, $C_1$-$C_6$-haloalkyl-$C_3$-$C_6$-halocycloalkyloxy, $C_3$-$C_6$-cycloalkyl-$C_1$-$C_6$-alkoxy, $C_3$-$C_6$-halocycloalkyl-$C_1$-$C_6$-alkoxy, $C_3$-$C_6$-cycloalkyl-$C_1$-$C_6$-haloalkoxy, $C_3$-$C_6$-halocycloalkyl-$C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, phenyl-$C_1$-$C_6$-alkoxy, phenyl-$C_1$-$C_6$-haloalkoxy, heterocyclyl-$C_1$-$C_6$-alkoxy, heterocyclyl-$C_1$-$C_6$-haloalkoxy, phenoxy, heterocyclyloxy, phenylcarbonyloxy, heterocyclylcarbonyloxy, phenylamino, heterocyclylamino, [N—($C_1$-$C_6$-alkyl), N-phenyl]amino, [N—($C_1$-$C_6$-alkyl), N—($C_3$-$C_6$-cycloalkyl)]amino, N—($C_3$-$C_6$-cycloalkyl)amino, N,N-di-($C_3$-$C_6$-cycloalkyl)amino, [N—($C_1$-$C_6$-alkyl), N—($C_3$-$C_6$-halocycloalkyl)]amino, [N—($C_1$-$C_6$-alkyl), N—($C_1$-$C_6$-haloalkyl)]amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, N—[($C_3$-$C_6$-cycloalkyl)-($C_1$-$C_6$-alkyl)]amino, N,N-di-[($C_3$-$C_6$-cycloalkyl)-($C_1$-$C_6$-alkyl)]amino, N—[($C_3$-$C_6$-halocycloalkyl)-($C_1$-$C_6$-alkyl)]amino, N—($C_1$-$C_6$-alkyl)-N—[($C_3$-$C_6$-cycloalkyl)-($C_1$-$C_6$-alkyl)]amino, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$-alkyl)amino, heterocyclyl, phenyl, the moiety of formula II,

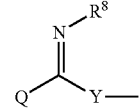

(II)

wherein
Q is hydrogen or $C_1$-$C_6$-alkyl;
Y is a direct bond or $C_1$-$C_6$-alkanediyl;
$R^8$ is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl)amino];
X is $OR^4$;
$R^4$ is hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_2$-$C_6$-alkenyloxy-$C_1$-$C_6$-alkyl, $C_2$-$C_6$-haloalkenyloxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkyl-aminocarbonyl-$C_1$-$C_6$-alkyl, N,N-di-($C_1$-$C_6$-alkyl)-aminocarbonyl-$C_1$-$C_6$-alkyl, [N—($C_3$-$C_6$-cycloalkyl-$C_1$-$C_6$-alkyl), N—($C_1$-$C_6$-alkyl)]aminocarbonyl-$C_1$-$C_6$-alkyl, $C_1$-$C_6$-alkoxy-aminocarbonyl-$C_1$-$C_6$-alkyl, $C_2$-$C_6$- alkenyl, $C_2$-$C_6$-haloalkenyl, $C_2$-$C_6$-alkynyl-$C_2$-$C_6$-alkenyl, $C_3$-$C_6$-alkynyl, $C_3$-$C_6$-haloalkynyl, heterocyclyl, phenyl, heterocyclylcarbonyl, phenylcarbonyl, heterocyclylcarbonyl-$C_1$-$C_6$-alkyl, phenylcarbonyl-$C_1$-$C_6$-alkyl, heterocyclyl-$C_1$-$C_6$-alkyl, phenyl-$C_1$-$C_6$-alkyl; wherein the phenyl and heterocyclyl moieties of $R^4$ and $R^5$ can be unsubstituted or substituted with one or more radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;
and their agriculturally useful salts;

More particularly useful as herbicides are those isoxazolo[5,4-b]pyridine compounds of formula I, wherein
$R^1$ is hydrogen;
$R^2$ is $C_3$-$C_6$-cycloalkyl, $C_3$-$C_6$-halocycloalkyl; most preferably cyclopropyl or 1-fluorocyclopropyl;
$R^3$ is $C_3$-$C_6$-cycloalkyloxy, $C_3$-$C_6$-halocycloalkyloxy, phenylamino, N—($C_3$-$C_6$-cycloalkyl)]amino;
X is $OR^4$;
$R^4$ is hydrogen, $C_1$-$C_6$-alkyl, $C_1$-$C_6$-haloalkyl, $C_1$-$C_6$-cyanoalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_3$-$C_6$-alkynyl.
and their agriculturally useful salts;

More particularly useful as herbicides are those isoxazolo[5,4-b]pyridine compounds of formula I, wherein
$R^1$ is hydrogen;
$R^2$ is $C_3$-$C_6$-cycloalkyl, $C_3$-$C_6$-halocycloalkyl; most preferably cyclopropyl or 1-fluorocyclopropyl;
$R^3$ is $C_3$-$C_6$-cycloalkyloxy, $C_3$-$C_6$-halocycloalkyloxy;
X is $OR^4$;
$R^4$ is hydrogen, $C_1$-$C_6$-alkyl, $C_1$-$C_6$-haloalkyl, $C_1$-$C_6$-cyanoalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_3$-$C_6$-alkynyl.
and their agriculturally useful salts;

Furthermore, useful as herbicides are those isoxazolo[5,4-b]pyridine compounds of formula I, wherein
$R^1$ is hydrogen;
$R^2$ is $C_3$-$C_6$-cycloalkyl, $C_3$-$C_6$-halocycloalkyl; most preferably cyclopropyl or 1-fluorocyclopropyl;
$R^3$ is $C_3$-$C_6$-cycloalkyloxy, $C_3$-$C_6$-halocycloalkyloxy, phenylamino, N—($C_3$-$C_6$-cycloalkyl)]amino;
X is $SR^5$;
$R^5$ is hydrogen, $C_1$-$C_6$-alkyl, $C_1$-$C_6$-haloalkyl, phenyl-$C_1$-$C_6$-alkyl; is most preferably $C_1$-$C_6$-alkyl, phenyl-$C_1$-$C_6$-alkyl.

Furthermore, useful as herbicides are those isoxazolo[5,4-b]pyridine compounds of formula I, wherein
$R^1$ is hydrogen;
$R^2$ is $C_3$-$C_6$-cycloalkyl, $C_3$-$C_6$-halocycloalkyl; most preferably cyclopropyl or 1-fluorocyclopropyl;
$R^3$ is $C_3$-$C_6$-cycloalkyloxy, $C_3$-$C_6$-halocycloalkyloxy;
X is $SR^5$;
$R^5$ is hydrogen, $C_1$-$C_6$-alkyl, $C_1$-$C_6$-haloalkyl, phenyl-$C_1$-$C_6$-alkyl; is most preferably $C_1$-$C_6$-alkyl, phenyl-$C_1$-$C_6$-alkyl.

Most particularly useful as herbicides are those isoxazolo[5,4-b]pyridine compounds of formula I, wherein
$R^1$ is hydrogen;
$R^2$ is cyclopropyl or 1-fluorocyclopropyl;
$R^3$ is $C_3$-$C_6$-cycloalkyloxy, $C_3$-$C_6$-halocycloalkyloxy, phenylamino, N—($C_3$-$C_6$-cycloalkyl)]amino;
X is $OR^4$;
$R^4$ is hydrogen;
and their agriculturally useful salts;

Most particularly useful as herbicides are also those isoxazolo[5,4-b]pyridine compounds of formula I, wherein
$R^1$ is hydrogen;
$R^2$ is cyclopropyl or 1-fluorocyclopropyl;
$R^3$ is $C_3$-$C_6$-cycloalkyloxy, $C_3$-$C_6$-halocycloalkyloxy, phenylamino, N—($C_3$-$C_6$-cycloalkyl)]amino;
X is $SR^5$;
$R^5$ is hydrogen, $C_1$-$C_6$-alkyl, $C_1$-$C_6$-haloalkyl, phenyl-$C_1$-$C_6$-alkyl; is most preferably $C_1$-$C_6$-alkyl, phenyl-$C_1$-$C_6$-alkyl.

The isoxazolo[5,4-b]pyridines of formula I according to the invention can be prepared by standard processes of organic chemistry, for example by the following processes:

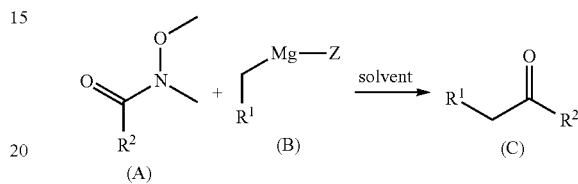

A compound of formula (C), where $R^1$ is $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-alkynyl or phenyl-$C_1$-$C_6$-alkyl, can be prepared by adding a compound of formula (B), where Z is a halogen, in an inert organic solvent at a temperature from −100° C. to 30° C., preferably at a temperature from −80° C. to 0° C., most preferably at −78° C., to a compound of formula (A) under an inert gas atmosphere such as argon or nitrogen. The reaction mixture is worked up in a customary manner, for example by mixing with water, separation of the phases, extraction and, if appropriate, chromatographic purification of the crude product, preferably by extraction.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl-ether, diisopropyl-ether, tert-butyl-methylether, dioxane, anisole and tetrahydrofuran, nitriles such as acetonitrile and propionitrile, as well as dimethylsulfoxide, dimethylformamide and N,N-dimethylacetamide or N-methylpyrrolidone.

Particular preference is given to tetrahydrofuran and diethyl ether. It is also possible to use mixtures of the solvents mentioned.

The compounds of formula (A) are known from the literature [Duncia, John V et al. Bioorganic & Medicinal Chemistry Letters 2008, 18(2), 576-585, and Gao, S. et al. Journal of the American Chemical Society 2010, 132(1), 371-383] or they can be prepared in accordance with the literature cited and/or are commercially available.

The compounds of formula (B) are commercially available.

A compound of formula (C), where $R^2$ is 1-fluorocyclopropyl and $R^1$ is hydrogen is known from the literature [DE 4206917].

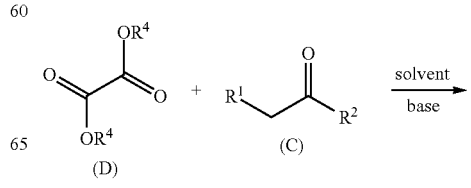

-continued

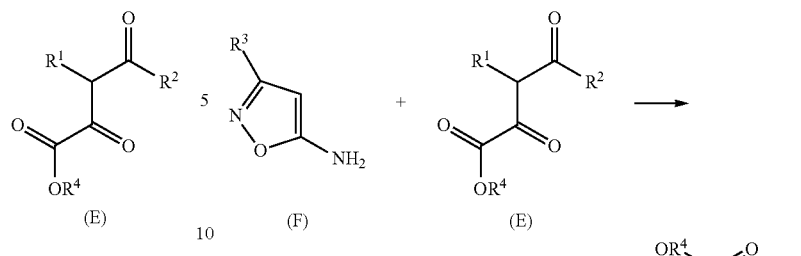

(E)          (F)          (E)

A compound of formula (E), where $R^4$ is $C_1$-$C_6$-alkyl and $R^1$ is hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-alkynyl or phenyl-$C_1$-$C_6$-alkyl may be prepared by treating a mixture of compounds (D) and (C) with a suitable base. The reaction is conducted in an inert organic solvent at a temperature from −100° C. to 100° C., preferably at a temperature from 0° C. to 80° C. The reaction mixture is worked up in a customary manner, for example by mixing with water, separation of the phases, extraction and, if appropriate, chromatographic purification of the crude product.

Suitable bases are in general inorganic compounds such as alkali metal and alkaline earth metal hydroxides such as lithium hydroxide, sodium hydroxide, potassium hydroxide and calcium hydroxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to sodium methoxide and sodium ethoxide.

The bases are generally employed in equimolar amounts or in excess.

Suitable solvents are ethers such as diethyl ether, diisopropyl ether, tert-butyl methylether, dioxane, anisole and tetrahydrofuran, nitriles such as acetonitrile and propionitrile, alkoholes such as methanol, ethanol, n-propanol, isopropanol, n-butanol and tert-butanol, as well as dimethylsulfoxide, dimethylformamide and N,N-dimethylacetamide or N-methylpyrrolidone.

Particular preference is given to methanol or ethanol. It is also possible to use mixtures of the solvents mentioned.

Suitable methods required for the preparation of compound of formula (E) are known from the literature [Brecker, L. et al., New J. Chem., 1999, 23, 437-446]. The substrates required for the preparation of compound of formula (E) are commercially available A compound of formula (E) where $R^1$ is halogen can be prepared according to suitable methods known from the literature [Cao, L. et al. Synlett 2009, 9, 1445-1448; Still, I. W. J. et al. Journal of Organic Chemistry 1981, 46(24), 4911-14 and Banks, R. E. et al. Journal of the Chemical Society, Chemical Communications 1994, 3, 343-344].

(G)

A compound of formula (G) can be prepared by mixing compound of formula (E) and compound of formula (F) in suitable solvent at a temperature of between 65° C. and 120° C., most preferably at 118° C. After the reaction is completed the reaction mixture is poured into ice/water. The solid formed is collected by filtration and dried under high vacuum.

Suitable solvents are
alkoholes such as methanol, ethanol, n-propanol, isopropanol, n-butanol and tert-butanol, water, carboxylic acids, such as formic acid, glacial acetic acid, as well as dimethylsulfoxide, dimethylformamide and N,N-dimethylacetamide or N-methylpyrrolidone.

Particular preference is given to glacial acetic acid.

It is also possible to use mixtures of the solvents mentioned.

Similar methods are described, for example, Petrosyan, V. A. et al. Russ. Chem. Bull., Int. Ed., 2007, 56, 2186-2188.

Suitable methods required for the preparation of compound of formula (F) are known from the literature [Scott, K. R. European Journal of Medicinal Chemistry 2002, 37, 635-648; Mitsuhashi, K. Journal of Heterocyclic Chemistry, 1986, 23(5), 1535-8; Safir, S. R. Journal of Organic Chemistry 1965, 30(8), 2862-4; Dines, M. B. Tetrahedron Letters 1969, 54, 4817-4819; Katsura, M. Nitriles. IV. Synthesis of isoxazoles and pyrazoles from some three-carbon nitriles, Takeda Kenkyushoho 1971, 30(3), 475-92; Bauer, L.; Nambury, C. N. V. Journal of Organic Chemistry 1961, 26, 4917-22; EP 0220947; WO 2008034008; WO 2010094120].

Some of the compounds of formula (F) are commercially available.

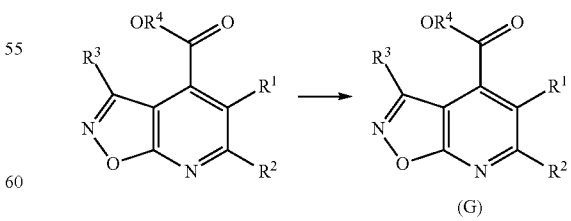

(G) $R_1$ = halogen (G)

A compound of formula (G) where $R^1$ is hydroxyl, $C_1$-$C_6$-alkoxy-$C_1$-$C_6$-alkyl, $C_1$-$C_6$-alkoxy, $C_1$-$C_6$-haloalkoxy can be prepared from a compound of formula (G) where $R^1$ is halogen according to suitable methods known from the literature, for example: Dejardin, J. V. et. al. Bulletin de la Societe Chimique de France 1976, 3-4, Pt. 2, 530-532, Ouyang, X. et. al. Bioorganic & Medicinal Chemistry Letters 2005, 15(23), 5154-5159 and Magee, T. V. et. al. Journal of Medicinal Chemistry 2009, 52(23), 7446-7457.

A compound of formula (G) where $R^1$ is hydrogen and $R^3$ is $C_3$-$C_6$-cycloalkyloxy, $C_3$-$C_6$-halocycloalkyloxy can be prepared by adding a $C_3$-$C_6$-(halo)cycloalkyl alcohol and a compound of formula (G) where $R^1$ is hydrogen and $R^3$ is OH with pyridine hydrohalide, acide (most preferably $H_3PO_4$) and phosphoroxyhalide and stirring it at a temperature between 50° C. and 120° C., most preferably at 90° C. for 1-5 h. The excess of phosphoroxyhalide is evaporated under high vacuum. The reaction mixture is worked up in a customary manner, for example by adding a suitable solvent and aqueus solution of alkali metal bicarbonate, separation of the phases, extraction and, if appropriate, chromatographic purification of the crude product.

Suitable solvents are ethyl acetate, dichloromethane, diethyl ether, chloroform, tertbuthylmethyl ether, diisopropyl ether. Suitable alkali metal bicarbonates are sodium bicarbonate, potassium bicarbonate, calcium bicarbonate.

A compound of formula (G) where $R^1$ is hydrogen and $R^3$ is $C_3$-$C_6$-cycloalkyloxy, $C_3$-$C_6$-halocycloalkyloxy can be prepared by adding a $C_1$-$C_6$-(halo)cycloalkyl alcohol and a compound of formula (G) where $R^1$ is hydrogen and $R^3$ is OH to the previously prepared stirred solution of di-$C_1$-$C_6$-alkyl azodicarboxylate and triarylphosphine (most preferably triphenylphosphine) in a suitable solvent (preferably tetrahydrofuran) at a temperature between -20° C. and 25° C., most preferably at 0° C. The reaction is conducted at a temperature between -20° C. to 100° C., preferably at a temperature between 40° C. to 80° C. The reaction mixture is worked up in a customary manner, for example by removing the solvent under vacuum and chromatographic purification of the crude product.

Suitable solvents are ethers such as diethyl-ether, diisopropyl-ether, tert-butyl-methylether, dioxane, anisole and tetrahydrofuran. Particular preference is given to tetrahydrofuran and diethyl ether. It is also possible to use mixtures of the solvents mentioned.

A compound of formula (G), where $R^3$ is $C_3$-$C_6$-alkenyloxy, $C_3$-$C_6$-alkynyloxy may be prepared by mixing a compound of formula (G) where $R^3$ is hydroxyl with WX where X is halogen and W is $C_3$-$C_6$-alkenyl, $C_3$-$C_6$-alkynyl. The reaction is usually carried out at from 0° C. to 120° C., preferably at from 20° C. to 50° C., in an inert organic solvent in the presence of a base. The reaction mixture is worked up in a customary manner, for example by adding a suitable solvent and aqueus solution of alkali metal bicarbonate, separation of the phases, extraction and, if appropriate, chromatographic purification of the crude product.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert-butyl methylether, dioxane, anisole and tetrahydrofuran, nitriles such as acetonitrile and propionitrile, ketones such as acetone, methyl ethyl ketone, diethyl ketone and tert-butyl methyl ketone, as well as dimethylsulfoxide, dimethylformamide and N,N-dimethylacetamide or N.methylpyrrolidone.

Particular preference is given to dimethylformamide.

It is also possible to use mixtures of the solvents mentioned.

Suitable bases are, in general inorganic compounds such as alkali metal and alkaline earth metal carbonates such as lithium carbonate, potassium carbonate and calcium carbonate, as well as alkali metal bicarbonates such as sodium bicarbonate, metal organic compounds, preferably alkali metal alkyls such as methyl lithium, butyl lithium, as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to potassium carbonate.

The bases are generally employed in catalytic amounts, however they can also be employed in equimolar amounts, in excess or, if appropriate, be used as solvent.

Suitable methods required for the preparation of compound of formula (G), where $R^3$ is phenylcarbonyloxy, phenyl-$C_1$-$C_6$-alkoxy, $C_1$-$C_6$-alkoxy-$C_1$-$C_6$-alkoxy, heterocyclyloxy are known from the literature [P. J. Kocienski, Protecting groups, Thieme, Stuttgart; 2005].

Suitable methods required for the preparation of compound of formula (G), where $R^3$ is phenoxy are known from the literature [Larock, R. C. Organic Letters 2004, 6(1), 99-102].

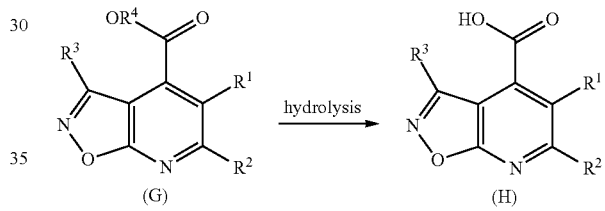

A compound of formula (H) can be prepared from a compound of formula (G) by hydrolysis in a presence of a suitable acid or base catalyst in a suitable solvent at temperatures between 0° C. and 80° C., most preferably at 25° C., under conventional heating or under microwave irradiation [see for example: Carrigan, C. N. J. Med. Chem. 2002, 45, 2260-2276 and Ghosh, P. Journal of Teaching and Research in Chemistry 2008, 15(2), 54-57].

Suitable acid catalysts are anorganic acids like hydrofluoric acid, hydrochloric acid, hydrobromic acid, perchloric acid, sulphuric acid.

Particular preference is given to hydrochloric acid and sulphuric acid.

The acids are generally employed in catalytic amounts, however they can also be employed in equimolar amounts or in excess.

Suitable base catalysts are alkali metal and alkaline earth metal hydroxides such as lithium hydroxide, sodium hydroxide, potassium hydroxide and calcium hydroxide.

Particular preference is given to metal hydroxides such as sodium hydroxide.

The bases are generally employed in catalytic amounts, however they can also be employed in equimolar amounts or in excess.

Suitable solvents are ethers such as diethyl ether, diisopropyl ether, tert-butyl methylether, dioxane, anisole and tetrahydrofuran, water, alkoholes such as methanol, ethanol, n-propanol, isopropanol, n-butanol and tert-butanol, as well as dimethylsulfoxide.

Particular preference is given to tetrahydrofuran.

It is also possible to use mixtures of the solvents mentioned.

A compound of formula (H), where $R^3$ is $C_1$-$C_6$-alkylthio, $C_3$-$C_6$-cycloalkylthio, $C_3$-$C_6$-halocycloalkylthio, $C_3$-$C_6$-cycloalkyl-$C_1$-$C_6$-alkylthio, $C_3$-$C_6$-halocycloalkyl-$C_1$-$C_6$-alkylthio, $C_3$-$C_6$-cycloalkyl-$C_1$-$C_6$-haloalkylthio, $C_3$-$C_6$-halocycloalkyl-$C_1$-$C_6$-haloalkylthio, heterocyclylthio, phenylthio, phenyl-$C_1$-$C_6$-alkylthio, heterocyclyl-$C_1$-$C_6$-alkylthio may be prepared in accordance with the literature cited: Larock, R. C. ACS Combinatorial Science 2011, 13(5), 501-510 or by mixing together compound (H), where $R^3$ is halogen with suitable thiol, palladium catalys, phosphine ligand and a base in a suitable solvent. The reaction is conducted in an inert organic solvent at a temperature from 0° C. to 100° C., preferably at a temperature from 25° C. to 85° C. The reaction mixture is worked up in a customary manner, for example by mixing with water, separation of the phases, extraction and, if appropriate, chromatographic purification of the crude product. Preference is given to palladium catalyst such as palladium(II) acetate, palladium (II) chloride, allylpalladium(II) chloride dimer, bis(benzonitrile) palladium(II) dichloride, bis(dibenzylideneacetone)palladium(0), [1,1'-bis(diphenylphosphino)ferrocene]palladium (II) dichloride dichloromethane adduct, bis (triphenylphosphine)palladium(II) dichloride, tetrakis (triphenylphosphine)palladium(0). Particular preference is given to palladium(II) acetate.

Suitable phosphine ligands are (2,2'-Bis(diphenylphosphino)-1,1'-binaphthyl), 1,1'-bis(diphenylphosphino)ferrocene, bis(2-diphenylphosphinophenyl)ether, di-t-butylmethylphosphonium tetrafluoroborate, 2-(Di-t-butylphosphino) biphenyl, tri-t-butylphosphonium tetrafluoroborate, tri-2-furylphosphine, tris(2,4-di-t-butylphenyl)phosphite, tri-o-tolylphosphine, (2R)-1-[(1R)-1-[bis(1,1-dimethylethyl) phosphino]ethyl]-2-(dicyclohexylphosphino)-ferrocene.

Particular preference is given to (2R)-1-[(1R)-1-[bis(1,1-dimethylethyl)phosphino]ethyl]-2-(dicyclohexylphosphino)-ferrocene.

Suitable bases are in general inorganic compounds such as, alkali metal and alkaline earth metal carbonates such as lithium carbonate, potassium carbonate and calcium carbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to potassium tert-butoxide.

The bases are generally employed in equimolar amounts or in excess.

Suitable solvents are ethers such as diethyl ether, diisopropyl ether, tert-butyl methylether, 1,2-dimethoxyethane, dioxane and tetrahydrofuran as well as aromatic hydrocarbons such as benzene, toluene, o-, m- and p-xylene.

Particular preference is given to 1,2-dimethoxyethane. It is also possible to use mixtures of the solvents mentioned.

A compound of formula (H), where $R^3$ is N—($C_1$-$C_6$-alkyl)amino, N—[($C_3$-$C_6$-cycloalkyl)-($C_1$-$C_6$-alkyl)]amino, N,N-di-($C_1$-$C_6$-alkyl)amino, N—($C_3$-$C_6$-cycloalkyl)-($C_1$-$C_6$-alkyl)amino phenylamino, N—($C_1$-$C_6$-alkyl)-N-phenylamino, [N—($C_1$-$C_6$-alkyl), N—($C_3$-$C_6$-cycloalkyl)]amino, ($C_3$-$C_6$-cycloalkyl)amino, N,N-di-($C_3$-$C_6$-cycloalkyl) amino, [N—($C_1$-$C_6$-alkyl), N—($C_3$-$C_6$-halocycloalkyl)] amino, ($C_3$-$C_6$-halocycloalkyl)amino, N,N-di-($C_3$-$C_6$-halocycloalkyl)amino, [N—($C_1$-$C_6$-alkyl), N-(phenyl-$C_1$-$C_6$-alkyl)]amino, (phenyl-$C_1$-$C_6$-alkyl)amino, (heterocyclyl-$C_1$-$C_6$-alkyl)amino, may be prepared by mixing suitable amine with compound of formula (H), where $R^3$ is halogen in the microwave at from 1 bar to 30 bar, preferably at from 5 bar to 10 bar, at a temperature of between 65° C. and 120° C., most preferably at 120° C. The reaction mixture is concentrated in vacuum and the residue is dissolved in suitable solvent, most preferably is diisopropyl ether. The solid formed is collected by filtration and dried under high vacuum.

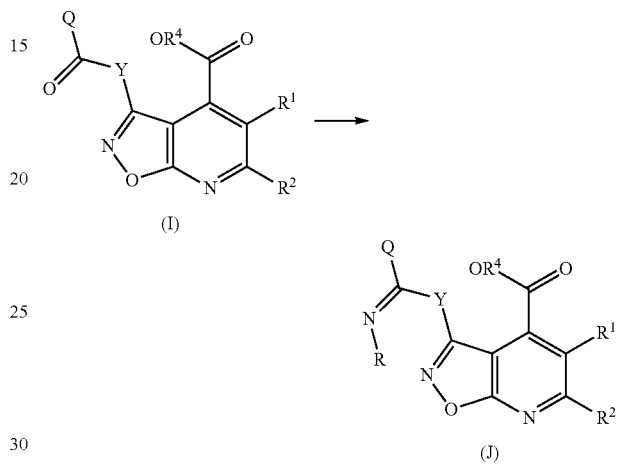

Suitable methods required for the preparation of compound of formula (J), where

Q is hydrogen or $C_1$-$C_6$-alkyl;

Y is a direct bond or $C_1$-$C_6$-alkanediyl;

R is amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino], or $C_1$-$C_6$-haloalkyl-[(aminocarbonyl) amino]; are known from the literature:

Stroh, H. H. Chemische Berichte 1957, 90, 352-7; Baltas, M. European Journal of Medicinal Chemistry 2010, 45(7), 3019-3026; Klein, D. X. Journal of Organic Chemistry 1957, 22, 951-4; Jayabalakrishnan, C. Journal of Coordination Chemistry 2010, 63(7), 1252-1262.

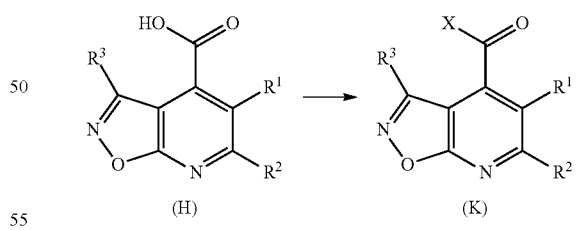

A compound of formula (H) can be esterified, thioesterified, transformed to an amide or an acid halide, preferably acid chloride, of a compound of formula (K) where X is $OR^4$ (see for example: Arnab, P. et. al. Angewandte Chemie, International Edition 2010, 49(8), 1492-1495), $SR^5$ (see for example: Silvestri, M. A. et. al. Journal of Medicinal Chemistry 2004, 47(12), 3149-3162), $NR^6R^7$ (see for example: Kuhn, B. et. al. Journal of Medicinal Chemistry 2010, 53(6), 2601-2611) under standard conditions.

The isoxazolo[5,4-b]pyridines of formula I are suitable as herbicides. They are suitable as such or as an appropriately formulated composition (herbicidal composition). As used in this application, the terms "formulated composition" and "herbicidal composition" are synonyms.

The herbicidal compositions comprising the isoxazolo[5,4-b]pyridines of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the isoxazolo[5,4-b]pyridines of formula I or compositions comprising them can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum*, (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera* and *Zea mays*.

Preferred crops are the following: *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum*, (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays*.

The isoxazolo[5,4-b]pyridines of formula I according to the invention can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are dis-closed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Furthermore, it has been found that the isoxazolo[5,4-b]pyridines of the formula I are also suitable for the defoliation and/or desiccation of plant parts, for which crop plants such as cotton, potato, oilseed rape, sunflower, soybean or field beans, in particular cotton, are suitable. In this regard, compositions for the desiccation and/or defoliation of plants, processes for preparing these compositions and methods for desiccating and/or defoliating plants using the isoxazolo[5,4-b]pyridines of formula I have been found.

As desiccants, the isoxazolo[5,4-b]pyridines of formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The isoxazolo[5,4-b]pyridines of formula I, or the herbicidal compositions comprising the isoxazolo[5,4-b]pyridines of formula I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one isoxazolo[5,4-b]pyridines of formula I and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol®23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations.

Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following:

mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqeuos solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water.

To prepare emulsions, pastes or oil dispersions, the isoxazolo[5,4-b]pyridines of formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the isoxazolo[5,4-b]pyridines of formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the isoxazolo[5,4-b]pyridines of formula I according to the present invention the active ingredients, e.g. the isoxazolo[5,4-b]pyridines of formula I, are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The isoxazolo[5,4-b]pyridines of formula I according to the present invention can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The isoxazolo[5,4-b]pyridines of formula I or the herbicidal compositions comprising them can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the isoxazolo[5,4-b]pyridines of formula I or the herbicidal compositions can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the isoxazolo[5,4-b]pyridines of formula I according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the active isoxazolo[5,4-b] pyridines of formula I according to the present invention (total amount of isoxazolo[5,4-b]pyridines of formula I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the isoxazolo[5,4-b]pyridines of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the isoxazolo[5,4-b]pyridines of formula I is 0.1 to 1000 g/ha, preferably 1 to 750 g/ha, more preferably 5 to 500 g/ha, of active substance.

To treat the seed, the isoxazolo[5,4-b]pyridines I are generally employed in amounts of from 0.001 to 10 kg per 100 kg of seed.

To widen the spectrum of action and to achieve synergistic effects, the isoxazolo[5,4-b]pyridines of the formula I may be mixed with a large number of representatives of other herbicidal or growth-regulating active ingredient groups and then applied concomitantly. Suitable components for mixtures are, for example, 1,2,4-thiadiazoles, 1,3, 4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-CF3-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may furthermore be beneficial to apply the isoxazolo[5,4-b]pyridines of formula I alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

Moreover, it may be useful to apply the isoxazolo[5,4-b]pyridines of formula I in combination with safeners. Safeners are chemical compounds which prevent or reduce damage on useful plants without having a major impact on the herbicidal action of the isoxazolo[5,4-b]pyridines of formula I towards unwanted plants. They can be applied either before sowings (e.g. on seed treatments, shoots or seedlings) or in the pre-emergence application or post-emergence application of the useful plant. The safeners and the isoxazolo[5,4-b]pyridines of formula I can be applied simultaneously or in succession.

Suitable safeners are, for example, (quinolin-8-oxy)acetic acids, 1-phenyl-5-haloalkyl-1H-1,2,4-triazole-3-carboxylic acids, 1-phenyl-4,5-dihydro-5-alkyl-1H-pyrazole-3,5-dicarboxylic acids, 4,5-dihydro-5,5-diary)-3-isoxazolecarboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzamides, 1,8-naphthalic anhydride, 2-halo-4-(haloalkyl)-5-thiazolecarboxylic acids, phosphorothioates, N-alkyl-O-phenylcarbamates and 2-oxo-nicotinamides and their agriculturally suitable salts, and, assuming that they have an acid function, their agriculturally suitable derivatives such as amides, esters and thioesters.

Hereinbelow, the preparation of representative isoxazolo[5,4-b]pyridines of formula I is illustrated by examples:
NMR spectra were recorded on a Bruker Avance II 300.
LC-MS were recorded on a Waters system with the following conditions:
Column: XTerra MS C$_{18}$ 5 µm (4.6×100 mm)
Gradient: from 95% H$_2$O/5% MeOH to 100% MeOH in 8 min
Flow: 1.5 mL/min
Alternatively, a Shimadzu Nexera UHPLC in combination with Shimadzu LCMS 20-20, ESI was used; column: Phenomenex Kinetex 1.7 µm XB-C18 100A;
ESI-MS
Mobile Phase: A (0.2% formic acid in water):B (methanol)=10:90, Flow Rate: 0.2 ml/min, Detection: ESI; Positive
HPLC
Column: YMC-Pack ODS-AQ, 50*4.6 mm I.D. S-5 µm, 12 nm
Mobile Phase: A: water(0.025% TFA), B: methanol; 6.0 min Flow Rate: 3 ml/min, Wavelength: 220/254 nm, Oven Tem: 40° C.

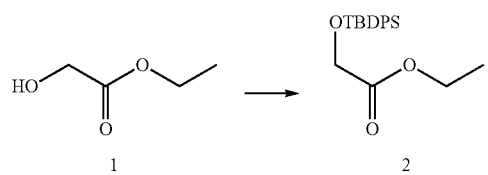

Synthesis of Compound 2

To a solution of compound 1 (200 g, 1.92 mol) in DCM (dichloromethane, 2 L) was added TBDPSi-Cl (tert-butyldiphenylsilyl chloride, 527 g, 1.92 mol) and the mixture was stirred at room temperature for 20 min until it dissolved. Then imidazole (261.9 g, 3.85 mol) was added portionwise over 20 min. The resulting mixture was stirred at room temperature for 5 h. To the mixture was added sat.NH$_4$Cl (2 L), and the aqueous layer extracted with DCM. The combined organics were washed with brine, dried over anhydrous Na$_2$SO$_4$ and concentrated in vacuum. The resulting crude product was purified by silica-gel column (petroleum ether:acetic acid ethyl ester (PE:AcOEt=80:1) to give 300 g of compound 2 (yield 47.6%).

$^1$H-NMR (CDCl$_3$): δ=7.68-7.70 (m, 4H), 7.26-7.43 (m, 6H), 4.23 (s, 2H), 4.14 (q, J=6.8 Hz, 2H), 1.22 (t, J=6.8 Hz, 3H), 1.09 (s, 9H).

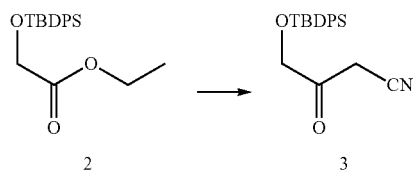

Synthesis of Compound 3

To 0.7 L THF (tetrahydrofurane) was added n-BuLi (2.5 M, 700 mL, 1.75 mol) at −78° C. under N2. At the same temperature, acetonitrile (72 g, 1.75 mol) in THF (300 mL) was added slowly dropwise. After stirring for 1 h at −78° C., a solution of compound 2 (300 g, 0.87 mol) in THF (300 mL) was added dropwise. The resulting solution was stirred from −78° C. for 3 h. The mixture was poured into ice water and acidified with 6N HCl to pH to 5-6. The THF layer was separated, and the aqueous layer was extracted with DCM. The combined organics were dried over anhydrous Na$_2$SO$_4$ and concentrated in vacuum. The resulting crude product (120 g) was used directly without further purification.

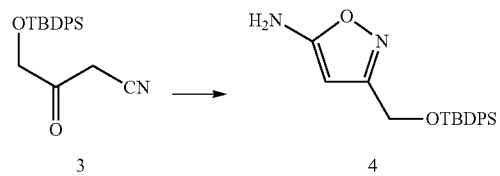

Synthesis of Compound 4

To a mixture of compound 3 (120 g, 0.35 mol) and NH$_2$OH—HCl (27.2 g, 0.39 mol) in DCM (2 L) was added NEt$_3$ (triethanolamine, 98.5 mL, 0.71 mol) under N2. The mixture was stirred at 50° C. for 12 h. Next it was poured into water and extracted with DCM. The combined organics were washed with brine, dried over anhydrous Na$_2$SO$_4$ and concentrated in vacuum. The resulting crude product was purified by silica-gel column (PE:AcOEt=20:1 to DCM:MeOH=80:1) to give 70 g of compound 4 (yield 55.9%).

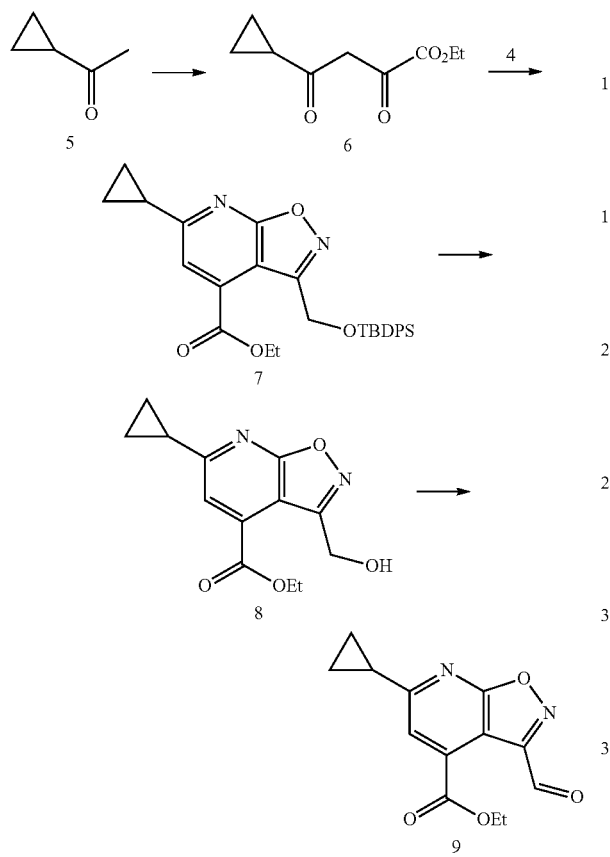

Synthesis of Compound 6

Metal Na (6 g, 0.26 mol) was added to ethanol (1.5 L) in portions and stirred until it dissolved. The above solution was cooled in an ice-water bath, and compound 5 (20 g, 0.24 mol) was added dropwise under N2 atmosphere. 0.5 h later, oxalic acid diethyl ester (31.6 g, 0.22 mol) was added dropwise at 0° C. with strong stirring. The resulting reaction mixture was stirred at room temperature overnight. The mixture was diluted with water and concentrated to remove ethanol on a rotary evaporator (water bath below 40° C.), and the residue was acidified to pH 2 by 6N aq. HCl and extracted with DCM. The combined extracts were washed with brine, dried over anhydrous Na$_2$SO$_4$ and concentrated on a rotary evaporator (water bath below 30° C.) to give compound 6 (21 g, yield: 48%).

$^1$H-NMR (CDCl$_3$): δ=6.47 (s, 1H), 4.37-4.32 (m, 2H), 1.92-1.86 (m, 1H), 1.37 (t, 3H, J=7.2 Hz), 1.24-1.04 (m, 4H).

Synthesis of Compound 7

A solution of compound 4 (70 g, 0.20 mol) and compound 6 (36.7 g, 0.20 mol) in AcOH (500 mL) were stirred at 100° C. for 2 h. The mixture was concentrated and purified by silica-gel column (PE:AcOEt=10:1), to give compound 7 (97 g, yield 97%).

Synthesis of Compound 8

To a solution of compound 7 (97 g, 0.19 mol) in THF (1.5 L) was added a solution of TBAF (tetra-n-butylammonium fluoride, 62.9 g, 0.29 mol) in THF (0.5 L) dropwise at room temperature. The resulting mixture was stirred at room temperature for 2 h. The mixture was diluted with AcOEt and washed with brine. The organic phase was dried over anhydrous Na$_2$SO$_4$ and concentrated in vacuum. The product was purified by silica-gel column (PE:AcOEt=1:1) to give compound 8 (32.9 g, yield 64.7%).

$^1$H-NMR (CDCl$_3$): δ=7.79 (s, 1H), 4.99 (s, 2H), 4.52 (q, J=7.2 Hz, 2H), 2.25 (m, 1H), 1.48 (t, J=7.2 Hz, 3H), 1.18-1.29 (m, 4H).

Synthesis of Compound 9

Oxalyl chloride (28.7 g, 0.22 mol) was added to DCM (800 mL) at −78° C. under N2, and then a solution of DMSO (dimethyl sulfoxide, 24 g, 0.31 mol) in DCM (500 mL) was added dropwise. The mixture was stirred at the same temperature for 1 h and a solution of compound 8 (32.9 g, 0.12 mol) in DCM (500 mL) was added dropwise and stirred at the same temperature for 2 h. NEt$_3$ (triethylamine, 173.9 g, 1.25 mol) was added dropwise to quench the reaction. The organic phase was washed with brine, dried over anhydrous Na$_2$SO$_4$ and concentrated in vacuum. The resulting crude product was purified by silica-gel column (PE:AcOEt=3:1) to give 9 (20.7 g, yield 63%).

$^1$H-NMR (CDCl$_3$): δ=10.42 (s, 1H), 7.65 (s, 1H), 4.88 (q, J=7.2 Hz, 2H), 2.2-2.3 (m, 1H), 1.40 (t, J=7.2 Hz, 3H), 1.20-1.30 (m, 4H).

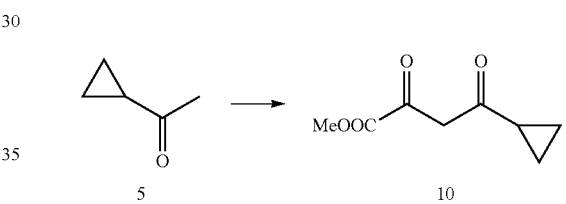

Synthesis of Compound 10

Na (14.67 g, 0.64 mol) was dissolved in dry methanol (0.8 L) and a solution of cyclopropylmethylketone 5 (50 g, 0.59 mol) and dimethyloxalate (70.2 g, 0.59 mol) in dry MeOH (0.2 L) was added dropwise at 0° C. The reaction mixture was stirred at room temperature 24 h and reflux overnight. Water (0.5 L) was added and the methanol was removed under reduced pressure. The aqueous solution was washed with Et$_2$O (150 mL), acidified to pH=2 with 2M H$_2$SO$_4$ and extracted with Et$_2$O (diethylether, 3×150 mL). The organic layer was dried over MgSO$_4$ and concentrated to dryness, to yield compound 10 (55.6 g, 55%), which was used without further purification.

$^1$H-NMR (CDCl$_3$): δ=14.61 (br, 1H), 6.84 (s, 1H), 3.90 (s, 3H), 1.95-1.82 (m, 1H), 1.26-1.20 (m, 2H), 1.10-1.00 (m, 2H).

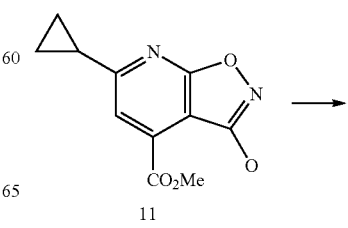

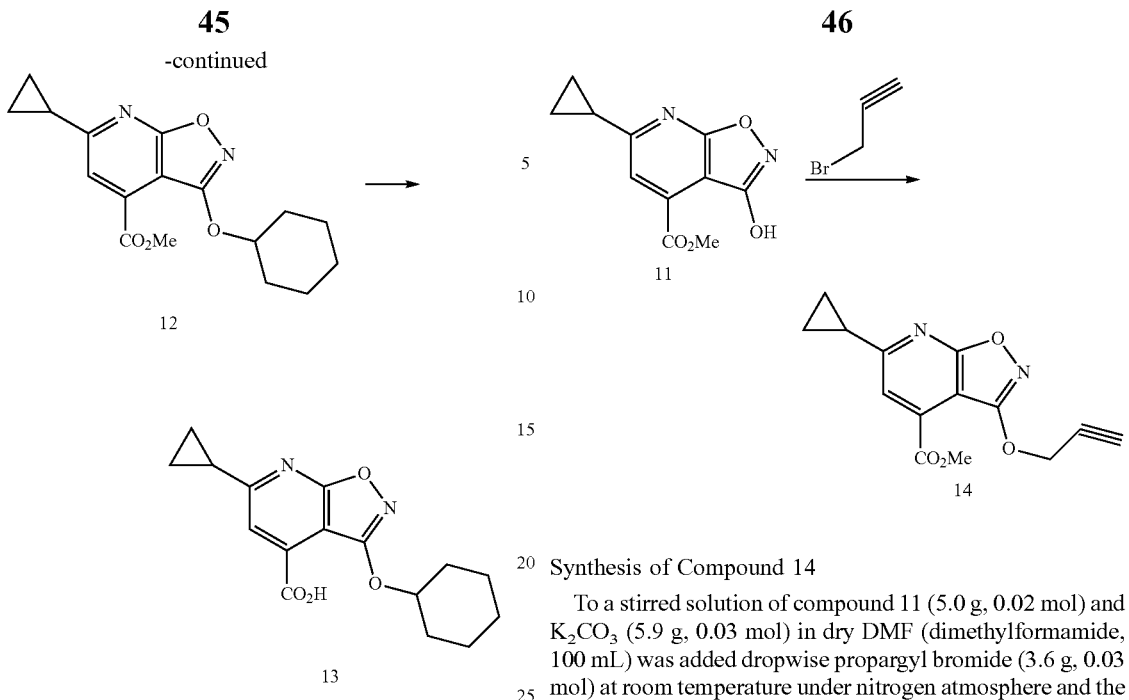

Synthesis of Compound 11

A mixture of compound 10 (17 g, 0.1 mol) and 5-aminoisoxazol-3-one (10 g, 0.1 mol) in acetic acid (AcOH) (100 mL) was stirred at reflux for 2 h. The reaction mixture was poured into ice/water (200 mL). The solid formed was collected by filtration and dried under high vacuum. 19 g (82%) of compound 11 were obtained.

$^1$H-NMR (CDCl$_3$): δ=10.30 (bs, 1H), 7.69 (s, 1H), 4.12 (s, 3H), 2.27-2.20 (m, 1H), 1.29-1.22 (m, 2H), 1.21-1.12 (m, 2H); MS: m/z=235 [M+H]+

Synthesis of Compound 12

To a stirred solution of triphenylphosphine (370 mg, 1.4 mmol) in dry THF (5 mL) was added dropwise diisopropyl azodicarboxylate (280 mg, 1.4 mmol) at 0° C. under nitrogen atmosphere and the mixture was stirred for 20 min. Then, cyclohexanol (130 mg, 1.3 mmol) and compound 11 (300 mg, 1.3 mmol) were added at 0° C. The mixture was stirred at room temperature for 2 h and heated to 40° C., stirred overnight. The mixture was cooled to room temperature and another portion of triphenylphosphine (370 mg, 1.4 mmol), cyclohexanol (130 mg, 1.3 mmol) and diisopropyl azodicarboxylate (280 mg, 1.4 mmol) were added. The mixture was stirred at room temperature for 1 h and heated to 60° C. and stirred overnight. The solvent was removed under reduced pressure. The residue was purified by column chromatography (SiO$_2$, c-Hex/AcOEt) to give compound 12 (320 mg, yield: 78%)

Synthesis of Compound 13

A solution of compound 12 (285 mg, 0.9 mmol) in a mixture 1:1 THF/1N NaOH (5 mL) was stirred at room temperature for 1.5 h. The reaction was concentrated in vacuum, the aqueous solution was acidified to pH 2 with 10% HCl and the solid formed was collected by filtration and dried under high vacuum to yield compound 13 (250 mg, 92%).

$^1$H-NMR (CDCl$_3$): δ=7.84 (s, 1H); 5.08-5.15 (m, 1H); 2.11-2.27 (m, 3H); 1.71-1.82 (m, 4H); 1.35-1.68 (m, 4H); 1.18-1.31 (m, 4H);

Synthesis of Compound 14

To a stirred solution of compound 11 (5.0 g, 0.02 mol) and K$_2$CO$_3$ (5.9 g, 0.03 mol) in dry DMF (dimethylformamide, 100 mL) was added dropwise propargyl bromide (3.6 g, 0.03 mol) at room temperature under nitrogen atmosphere and the mixture was stirred for 2 h. The solvent was removed in vacuum and the residue partitioned between AcOEt and water. The organic layer was washed with brine, dried over anhydrous Na$_2$SO$_4$ and concentrated in vacuum. The resulting crude product was purified by silica-gel column (c-Hexan:AcOEt=10:1) to give 14 (2.5 g, yield 43%).

$^1$H-NMR (DMSO): σ=7.65 (s, 1H); 5.09 (s, 2H); 4.50 (q, 2H); 2.61 (s, 1H); 2.25-2.15 (m, 1H); 1.46 (t, 3H); 1.10-1.30 (m, 4H); LCMS: 1.196 min, m/z=287 [M+H]+

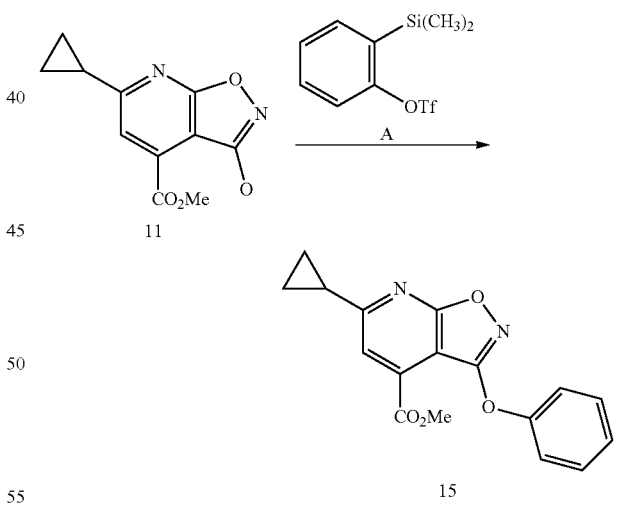

Synthesis of Compound 15

To a solution of MeCN (80 mL), compound 11 (1.0 g, 0.004 mol) and the silylaryl triflate A (2.0 g, 0.006 mol) was added CsF (2.0 g, 0.014 mol). The reaction mixture was allowed to stir at room temperature for 24 h and the resulting solution was washed with brine (20 mL) and extracted with AcOEt (20 mL). The combined ether fractions were dried over Na$_2$SO$_4$ and concentrated under reduced pressure. The residue was purified by flash chromatography on silica gel to afford the desired product 15 (0.9 g, 67% yield).

¹H-NMR (DMSO): σ=7.78-7.80 (d, J=8.01 Hz, 2H); 7.76 (s, 1H); 7.54 (t, J=8.0 Hz, 2H); 7.34 (t, J=8.0 Hz, 1H); 3.34 (s, 3H); 2.41-2.46 (m, 1H); 1.11-1.24 (m, 4H); LCMS: 3.608 min, m/z=311 [M+H]+

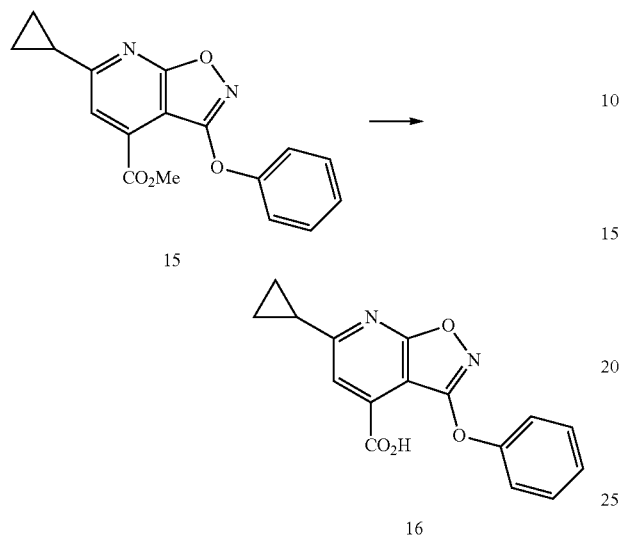

Synthesis of Compound 16

To a solution of compound 15 (0.9 g, 0.003 mol) in a mixture 1:1 THF/H₂O (20 mL) was added a solution of LiOH (0.3 g, 0.012 mol) in H₂O (5 mL). The reaction mixture was stirred at room temperature for 1.5 h. The reaction was concentrated in vacuum, the aqueous solution was acidified to pH 2 with 10% HCl and the solid formed was collected by filtration and dried under high vacuum to yield compound 16 (0.3 g, 33%).

¹H-NMR (CD3)2CO: σ=7.99 (s, 1H); 7.93-7.95 (m, 2H); 7.63 (t, 2H); 7.47 (t, 1H); 2.50-2.60 (m, 1H); 1.22-1.33 (m, 4H).

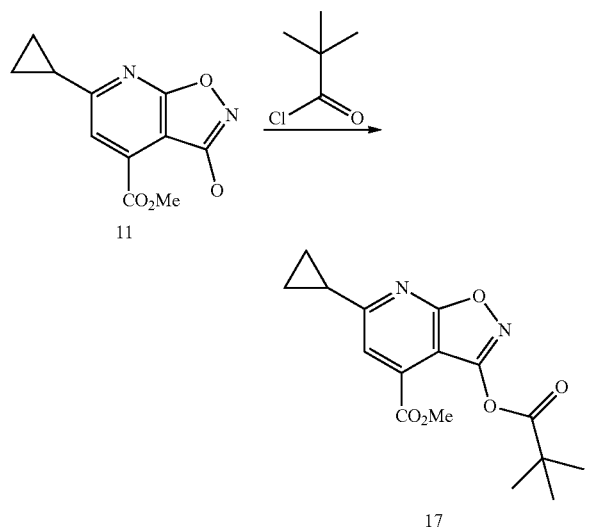

Synthesis of Compound 17

To a stirred solution of compound 11 (1.0 g, 0.004 mol) and NEt₃ (0.6 g, 0.006 mol) in dry DCM (20 mL) was added dropwise pivalic acid chloride (3.6 g, 0.004 mol) at 0° C. under nitrogen atmosphere. The reaction mixture was stirred at room temperature for 2 h. The solvent was removed in vacuum and the residue partitioned between AcOEt and water. The organic layer was washed with the aqueous solution of 5% HCl and water, dried over Na₂SO₄ and concentrated in vacuum to give 17 (1.2 g, yield 88%).

¹H-NMR (DMSO): σ=7.70 (s, 1H); 3.94 (s, 3H); 2.26-2.16 (m, 1H); 1.45 (s, 9H); 1.30-1.16 (m, 4H); LCMS: 3.868 min, m/z=235 [M-tBuCO+H]+

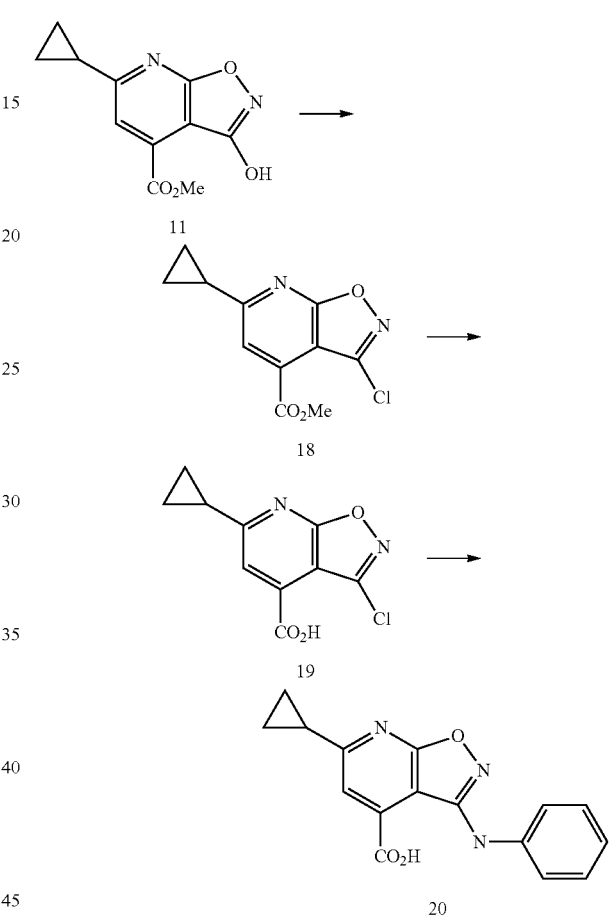

Synthesis of Compound 18

A mixture of compound 11 (12.0 g, 0.05 mol), pyridine hydrochloride (20.0 g, 0.17 mol), H₃PO₄ (3.6 g, 0.04 mol) and POCl₃ (120 mL) was stirred at 90° C. for 3 h. The excess of POCl₃ was evaporated under high vacuum. Remaining mixture was dissolved in ethyl acetate and slowly neutralized with NaHCO₃ at 0° C. The organic layer was washed with brine and water, dried over MgSO₄ and concentrated to dryness. The residue was purified by column chromatography (SiO₂, c-Hex/AcOEt) to give compound 18 (6.5 g, yield: 50%).

¹H-NMR (CDCl₃): δ=7.72 (s, 1H), 4.05 (s, 3H), 2.29-2.20 (m, 1H), 1.32-1.26 (m, 2H), 1.25-1.18 (m, 2H); MS: m/z=253 [M+H]+

Synthesis of Compound 19

To a solution of compound 18 (9.3 g, 0.035 mol) in a mixture 1:1 THF/H₂O (100 mL) was added a solution of LiOH (1.0 g, 0.041 mol) in H₂O (15 mL). The reaction mixture was stirred at room temperature for 1.5 h. The reaction was concentrated in vacuum, the aqueous solution was acidified to pH 2 with 10% HCl and the solid formed was collected by filtration and dried under high vacuum to yield compound 19 (8.3 g, 99%).

$^1$H-NMR (CDCl$_3$): δ=9.50-9.70 (bs, 1H), 7.61 (s, 1H) 2.85 (s, 3H), 2.28-2.19 (m, 1H), 1.30-1.10 (m, 2H); LCMS: 1.099 min, m/z=239 [M+H]+

Synthesis of Compound 20

Compound 19 (500 mg, 2.1 mmol) and aniline (5 mL) were stirred in the microwave at 10 bar, 120° C. for 1 h. The reaction was concentrated in vacuum and the residue was dissolved in diisopropyl ether. The solid formed was collected by filtration and dried under high vacuum to yield compound 20 (300 mg, 48%).

$^1$H-NMR (DMSO): δ=23.35 (s, 1H); 11.9 (bs, 1H) 7.69 (s, 1H); 7.56-7.50 (m, 2H); 7.35 (t, 2H); 6.93 (t, 1H); 2.35-2.26 (m, 1H); 1.00-1.10 (m, 4H); LCMS: 1.335 min, m/z=296 [M+H]+

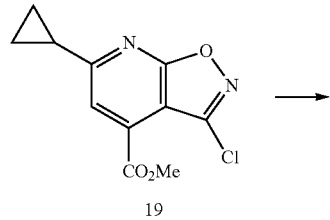

Synthesis of Compound 21

Compound 19 (500 mg, 2.1 mmol) and cyclopropylamine (5 mL) were stirred in the microwave at 5 bar, 120° C. for 1 h. The reaction was concentrated in vacuum and purified by preparative HPLC to give compound 21 (65 mg, 12%).

$^1$H-NMR (DMSO): δ=7.75 (s, 1H); 7.28 (s, 1H); 2.70-2.58 (m, 1H); 2.42-2.35 (m, 1H); 1.18-1.00 (m, 4H); 0.80-0.70 (m, 2H); 0.51-0.59 (m, 2H); LCMS: 2.489 min, m/z=260 [M+H]+

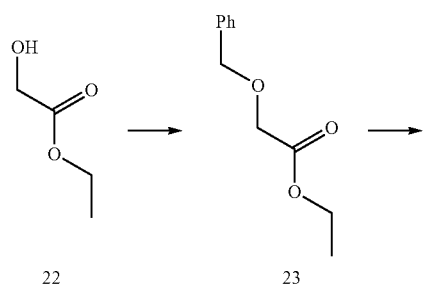

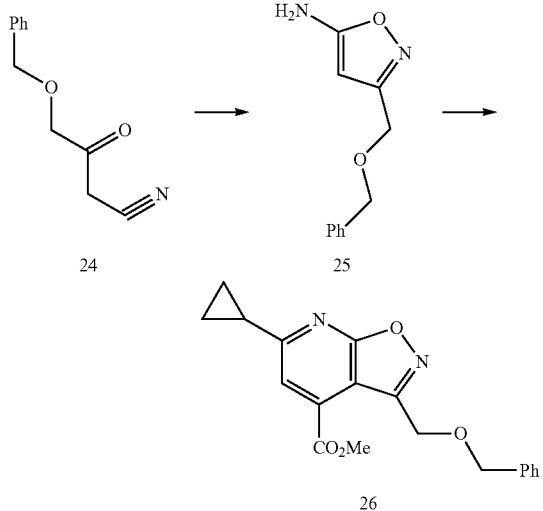

Synthesis of Compound 23

To the solution of hydroxy-acetic acid ethyl ester 22 (99.6 g, 0.96 mol) in THF (1.5 L) under nitrogen atmosphere, NaH (42.0 g, 1.0 mol: 60% in mineral oil) was added at 0° C. in portions. The mixture was stirred at 0° C. for 30 min and tetrabutylammonium iodide (35.3 g, 0.10 mol) and benzyl bromide (163.6 g, 0.96 mol) were added. The mixture was allowed to warm up to room temperature and was stirred in this temperature for 12 h. The reaction mixture was diluted with water and extracted with ethyl acetate. The organic layer was dried over MgSO$_4$, solvent was evaporated under high vacuum and raw product was distilled (121° C./4 mBar) to give compound 23 (135.5 g, yield: 73%).

$^1$H-NMR (CDCl$_3$): δ=7.41-7.22 (m, 5H), 4.65 (s, 2H), 4.27 (q, 2H), 4.11 (s, 2H), 1.25 (t, 3H).

Synthesis of Compound 24

Tetrahydrofuran (1 L) and NaH (30.0 g, 0.77 mol: 60% in mineral oil) were stirred under nitrogen atmosphere and heated to 50° C. To this mixture, a tetrahydrofuran solution of compound 23 (135.5 g, 0.70 mol) and acetonitrile (37.1 g, 0.90 mol) were added. The reaction was stirred at room temperature for 12 h. The reaction mixture was diluted with water and extracted with MTBE (Methyl tert-butyl ether). The water phase was acidified with citric acid (pH=3) and extracted with ethyl acetate. The organic layer was washed with brine and water, dried over MgSO$_4$ and concentrated to dryness. The residue was purified by column chromatography (SiO$_2$, c-Hex/AcOEt) to give compound 24 (41 g, yield: 31%)

$^1$H-NMR (CDCl$_3$): δ=7.40-7.21 (m, 5H), 4.58 (s, 2H), 4.10 (s, 2H), 3.61 (s, 2H).

Synthesis of Compound 25

A mixture of compound 24 (63.3 g, 0.33 mol), hydroxylamine hydrochloride (30.2 g, 0.43 mol) and sodium acetate (82.3 g, 1 mol) in EtOH (1 L) was stirred at room temperature for 4 h. Solvent was removed under high vacuum. The reaction mixture was poured into water and extracted with methylene chloride. The organic layer was washed with brine and water, dried over MgSO$_4$ and concentrated to dryness. The residue was purified by column chromatography (SiO$_2$, c-Hex/AcOEt) to give compound 25 (13.8 g, yield: 20%).

$^1$H-NMR (CDCl$_3$): δ=7.40-7.22 (m, 5H), 5.20 (s, 1H), 4.55 (bs, 4H), 4.46 (s, 2H).

Synthesis of Compound 26

A mixture of compound 10 (11.5 g, 0.07 mol) and 25 (13.8 g, 0.07 mol) in AcOH (150 mL) was stirred at reflux for 2 h. The reaction mixture was poured into ice/water (200 mL). The solid formed was collected by filtration and dried under high vacuum. 16.5 g (72%) of compound 26 were obtained.

$^1$H-NMR (CDCl$_3$): δ=7.68 (s, 1H), 7.32 (s, 5H), 5.03 (s, 2H), 4.60 (s, 2H), 3.95 (s, 3H), 2.26-2.20 (m, 1H), 1.30-1.25 (m, 2H), 1.20-1.12 (m, 2H); MS: m/z=339 [M+H]+

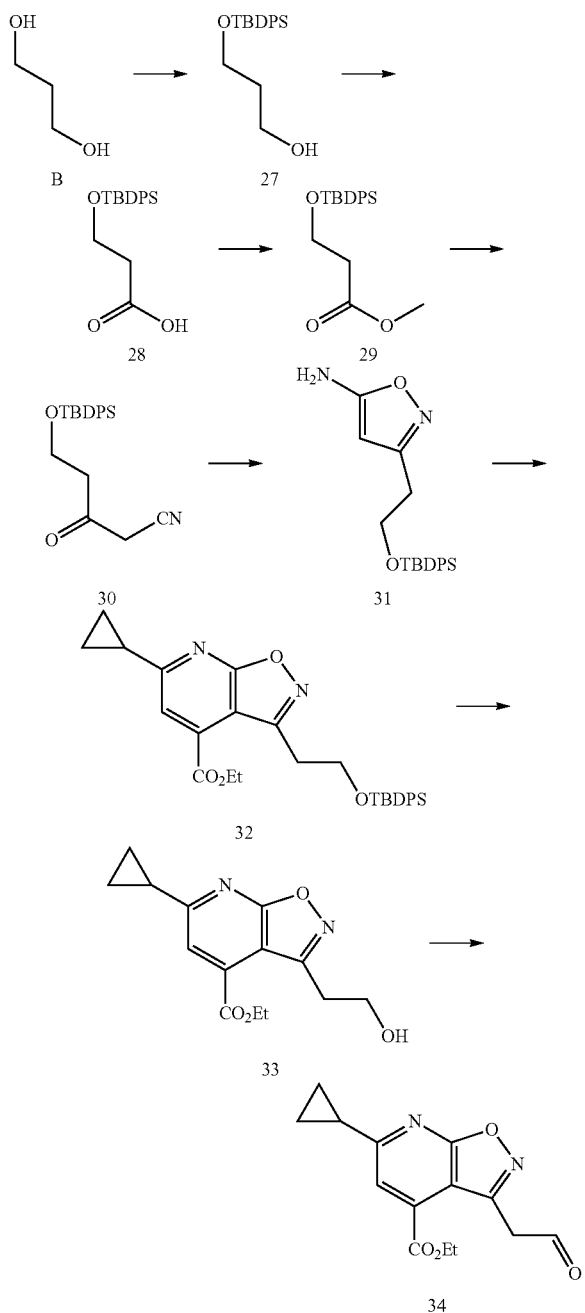

Synthesis of Compound 27

To a solution of propane-1,3-diol B (304 g, 4 mol) in 3 L dry DCM was added Et$_3$N (1212 g, 12 mol) and TBDPSiCl (548 g, 2 mol) and the mixture stirred at 20° C. for 16 h. The mixture was washed with brine, dried, concentrated and purified by silica gel column (PE:AcOEt=1000:1) to afford the product compound 27 (300 g, yield 47.8%).

$^1$H-NMR (CDCl$_3$): δ=7.66-7.68 (m, 4H), 7.39-7.43 (m, 6H), 3.82-3.85 (m, 4H), 1.80-1.81 (m, 2H), 1.04 (s, 9H).

Synthesis of Compound 28

To a solution of compound 27 (278 g, 0.88 mol) in 3 L dry acetone was added Jones Reagent (148.7 g CrO$_3$ in 128 mL conc. H$_2$SO$_4$ and 557 mL H$_2$O) dropwise at 0° C. and stirred at 0° C. for 16 h. The solvent was removed in vacuum and the residue partitioned between EtOAc and water. The organic layer was washed with brine, dried and concentrated to afford the product compound 28 (289 g, 87.8%).

$^1$H-NMR (CDCl$_3$): δ=7.66-7.68 (m, 4H), 7.38-7.43 (m, 6H), 3.94 (t, J=6.8 Hz, 2H), 2.60 (t, Hz, 2H), 1.04 (s, 9H).

Synthesis of Compound 29

To a solution of compound 28 (180 g, 0.549 mol) in 2 L dry DMF was added K$_2$CO$_3$ (151.8 g, 1.098 mol) and then CH$_3$I (90.5 g, 0.604 mol). The mixture was stirred at 20° C. for 16 h. The solvent was removed and the residue was purified by silica gel column (PE:AcOEt=100:1) to afford compound 29 (170 g, yield 90.6%).

$^1$H-NMR (CDCl$_3$): δ=7.65-7.68 (m, 4H), 7.38-7.43 (m, 6H), 3.95 (t, J=6.8 Hz, 2H), 3.68 (s, 3H), 2.61 (t, Hz, 2H), 1.03 (s, 9H).

Synthesis of Compound 30

To a solution of n-BuLi (487 mL, 1.264 mol) in 3 L THF was added CH$_3$CN (50 g, 1.264 mol) in 100 mL THF dropwise at −78° C. under N2 and stirred for 2 h. Then compound 29 (300 g, 0.843 mol) was added slowly and the mixture stirred at −78° C.~20° C. for 5 h. The mixture was poured into ice-water, acidified with 6N aqueous HCl to pH 3, extracted with AcOEt. The organic layer was purified by silica gel column (PE:AcOEt=100:1) to afford compound 30 (200 g, yield 64.9%).

$^1$H-NMR (CDCl$_3$): δ=7.62-7.72 (m, 4H), 7.37-7.45 (m, 6H), 3.95 (t, J=6.8 Hz, 2H), 3.53 (s, 3H), 2.75 (t, Hz, 2H), 1.04 (s, 9H).

Synthesis of Compound 31

To a mixture of compound 30 (170 g, 0.484 mol) and NH$_2$OH—HCl (34.4 g, 0.484 mol) in 2 L DCM was added Et$_3$N (73.3 g, 0.726 mol) dropwise at 0° C. and the mixture was heated at reflux for 5 h. The mixture was washed with brine, dried and concentrated to afford the compound 31 (120 g, yield 70.6%).

$^1$H-NMR (CDCl$_3$): δ=7.62-7.72 (m, 4H), 7.37-7.45 (m, 6H), 3.95 (t, J=6.8 Hz, 2H), 3.53 (s, 3H), 2.75 (t, Hz, 2H), 1.04 (s, 9H).

Synthesis of Compound 32

To a solution of compound 31 (120 g, 0.328 mol) in 1500 mL AcOH was added compound 6 (60.3 g, 0.328 mol) dropwise at 20° C. and the mixture was heated at reflux for 5 h. The solvent was removed and the residue was partitioned between AcOEt and water. The combined organics were washed with brine, dried and concentrated to afford compound 32 (170 g, yield 100%).

$^1$H-NMR (CDCl$_3$): δ=7.62 (s, 1H), 7.28-7.55 (m, 10H), 4.38 (q, 2H), 4.05 (t, J=6.8 Hz, 2H), 3.45 (t, Hz, 2H), 2.22 (m, 1H), 1.38 (m, 3H), 1.15-1.28 (m, 4H), 0.99 (s, 9H).

Synthesis of Compound 33

To a solution of compound 32 (170 g, 0.331 mol) in 2 L THF was added a solution of TBAF (129.5 g, 0.496 mol) in 300 mL THF dropwise and the mixture was stirred at 20° C. for 15 h. The solvent was removed and the residue was purified by silica gel column (PE:AcOEt=10:1) to afford compound 33 (78 g, yield 85.7%).

$^1$H-NMR (CDCl$_3$): δ=7.68 (s, 1H), 4.46 (q, Hz, 2H), 4.10 (t, Hz, 2H), 3.41 (t, Hz, 2H), 2.32 (m, 1H), 1.45 (t, J=7.2 Hz, 3H), 1.22-1.26 (m, 4H).

Synthesis of Compound 34

To a solution of compound 33 (45 g, 0.163 mol) in 2 L DCM was added DessMartin periodinane (103.6 g, 0.244 mol) and the mixture was stirred at 20° C. for 15 h. The solvent was removed and the residue was purified on silica gel column (PE:AcOEt=5:1) to afford the product 34 (38 g, 83.0%).

$^1$H-NMR (CDCl$_3$): δ=9.87 (s, 1H), 7.72 (s, 1H), 4.41 (q, J=7.2 Hz, 2H), 3.45 (s, 1H), 2.23 (m, 1H), 1.40 (t, J=7.2 Hz, 3H), 1.16-1.28 (m, 4H).

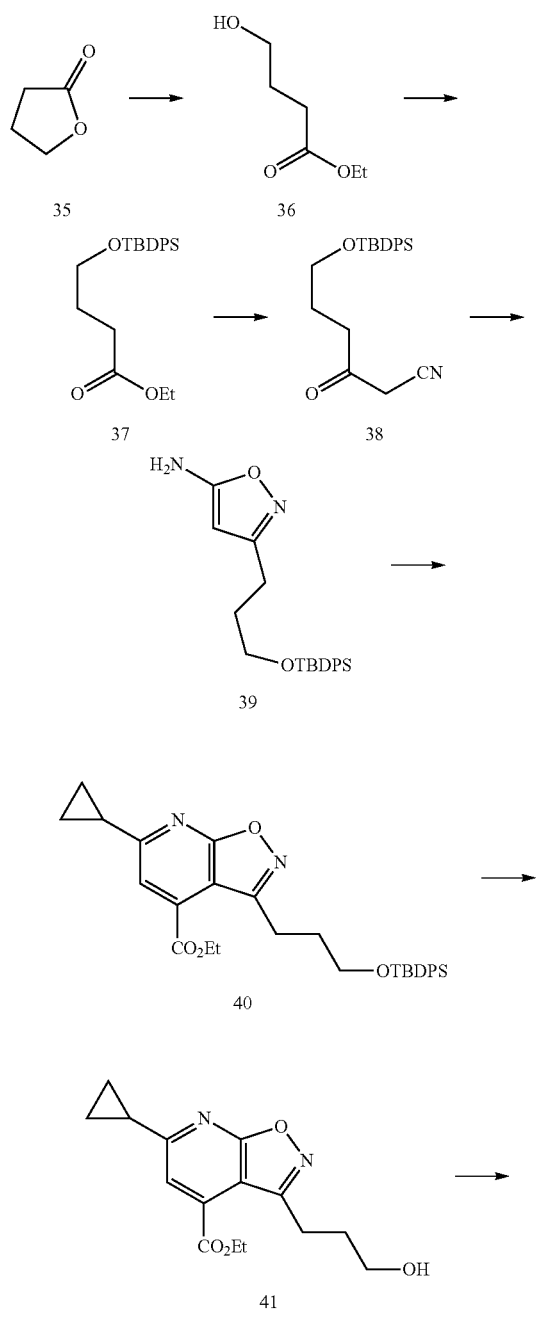

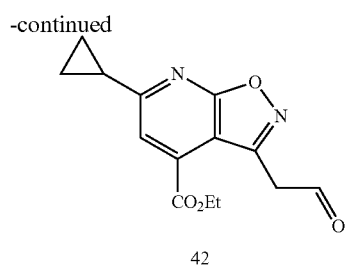

Synthesis of Compound 36

A mixture of compound 35 (258 g, 3 mol) and EtONa (16.2 g, 0.3 mol) in 3 L EtOH was stirred at 20° C. for 48 h. The mixture was concentrated and the residue was treated with DCM and the solid was filtered off. The filtrate was dried and concentrated to afford the crude product compound 36 (150 g, 21.4%).

$^1$H-NMR (CDCl$_3$): δ=4.11 (q, Hz, 2H), 3.62 (m, 2H), 2.48 (m, 2H), 1.81-1.86 (m, 2H), 1.17 (t, Hz, 3H).

Synthesis of Compound 37

To a solution of compound 36 (132 g, 1 mol) in 1.5 L DCM was added imidazole (81.6 g, 1.2 mol) and then TBDPSiCl (274 g, 1 mol) was added dropwise. The mixture was stirred at 20° C. for 16 h. The mixture was concentrated and the residue was purified by silica gel column (PE:AcOEt=500:1) to afford the product compound 37 (300 g, yield 81.1%).

$^1$H-NMR (CDCl$_3$): δ=7.36-7.73 (m, 10H), 4.11 (q, J=7.2 Hz, 2H), 3.69 (t, J=6.4 Hz, 2H), 2.45 (t, J=7.6 Hz, 2H), 1.85-1.92 (m, 2H), 1.24 (t, Hz, 3H), 0.87 (s, 9H).

Synthesis of Compound 38

To a solution of n-BuLi (487 mL, 1.216 mol) in 3 L THF was added CH$_3$CN (50 g, 1.216 mol) in 100 mL THF dropwise at −78° C. under N2 and stirred for 2 h. Then compound 37 (300 g, 0.811 mol) was added slowly and stirred at −78° C. to 20° C. for 5 h. The mixture was poured into water, acidified with 6N aqueous HCl to pH 3, extracted with AcOEt. The organic layer was purified by silica gel column (PE:AcOEt=100:1) to afford the product compound 38 (250 g, yield 84.5%).

$^1$H-NMR (CDCl$_3$): δ=7.39-7.74 (m, 10H), 3.70 (t, J=6.0 Hz, 2H), 3.39 (s, 2H), 2.71 (t, Hz, 2H), 1.85-1.90 (m, 2H), 1.24 (t, Hz, 3H), 1.07 (s, 9H).

Synthesis of Compound 39

To a mixture of compound 38 (190 g, 0.52 mol) and NH$_2$OH—HCl (55.4 g, 0.78 mol) in 2 L DCM was added Et$_3$N (78.9 g, 0.78 mol) dropwise at 0° C. and the mixture was heated at reflux for 5 h. The mixture was washed with brine, dried and concentrated to afford the product compound 39 (185 g, yield 93.6%).

$^1$H-NMR (CDCl$_3$): δ=7.65-7.67 (m, 4H), 7.36-7.44 (m, 6H), 4.92 (s, 1H), 3.72 (t, Hz, 2H), 2.63 (t, Hz, 2H), 1.04 (s, 9H).

Synthesis of Compound 40

To a solution of compound 39 (190 g, 0.50 mol) in 1 L AcOH was added compound 6 (92 g, 0.50 mol) dropwise at 20° C. and the mixture heated at reflux for 5 h. The solvent was removed and the residue was treated with AcOEt and water. The combined organics were washed with brine, dried and concentrated to afford the product compound 40 (200 g, yield 75.8%).

$^1$H-NMR (CDCl$_3$): δ=7.64-7.66 (m, 4H), 7.32-7.39 (m, 6H), 4.43 (q, J=7.2 Hz, 2H), 3.79 (t, J=6.4 Hz, 2H), 3.25 (t, Hz, 2H), 2.22 (m, 1H), 2.04 (m, 1H), 1.43 (t, 3H), 1.15-1.28 (m, 4H), 1.14-1.17 (m, 4H), 1.07 (s, 9H).

Synthesis of Compound 41

To a solution of compound 40 (200 g, 0.379 mol) in 2 L THF was added TBAF (148.3 g, 0.568 mol) in 300 mL THF dropwise and the mixture was stirred at 20° C. for 15 h. The solvent was removed and the residue was purified by silica gel column (PE:AcOEt=5:1) to afford the product compound 41 (50 g, yield 45.5%).

$^1$H-NMR (CDCl$_3$): δ=7.68 (s, 1H), 4.48 (q, Hz, 2H), 3.75 (t, Hz, 2H), 3.27 (t, J=7.2 Hz, 2H), 2.21 (m, 1H), 2.06 (m, 2H), 1.46 (t, Hz, 3H), 1.14-1.27 (m, 4H).

Synthesis of Compound 42

To a solution of oxalyl chloride (43.8 g, 0.344 mol) in 1 L DCM was added DMSO (26.9 g, 0.344 mol) dropwise at −78° C. under N2 and stirred for 1 h. Then compound 41 (50 g, 0.172 mol) in 100 mL DCM was added dropwise at −78° C. and stirred for 2 h. Then Et$_3$N (173.7 g, 1.72 mol) was added dropwise and stirred at −78° C.~20° C. for 2 h. The mixture was quenched with sat. NH$_4$Cl and the organic layer washed with brine, and purified by silica gel column (PE: AcOEt=5:1) to afford the product 42 (14.3 g, yield 28.9%).

$^1$H-NMR (CDCl$_3$): δ=9.92 (s, 1H), 7.71 (s, 1H), 4.48 (q, J=7.2 Hz, 2H), 3.48 (t, J=7.2 Hz, 2H), 3.06 (t, J=7.2 Hz, 2H), 2.24 (m, 1H), 1.47 (t, Hz, 3H), 1.16-1.27 (m, 4H).

The isoxazolo[5,4-b]pyridines according to table 3 below were prepared in accordance with the methods described above;

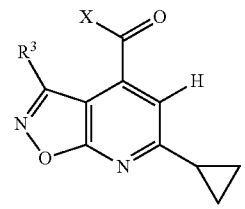

I.a

TABLE 3

| cpd.-no | R$^3$ | X | R. T. (min) | m/z = [M + H]+ | m.p. (° C.) |
|---|---|---|---|---|---|
| I.a.41. | —O(CO)C(CH$_3$)$_3$ example not according to the invention | —OCH$_3$ | 3.861 | 235 [M-tBuCO + H]+ | 58 |
| I.a.42. | —O(CO)C(CH$_3$)$_3$ example not according to the invention | —OH | 1.843 | 221 [M-tBuCO + H]+ | 246 |
| I.a.43. | —O(CO)C$_6$H$_5$ | —OCH$_3$ | 4.004 | 339 | 127 |
| I.a.44. | —OCH$_2$CHCH$_2$ | —OH | 1.095 | 261 | 153 |
| I.a.45. | —OCH$_2$OCH$_3$ | —OH | 0.999 | 265 | 147 |
| I.a.46. | —OC$_6$H$_5$ | —OH | | | 223 |
| I.a.47. | —CHNOH | —OCH$_3$ | 0.988 | 262 | |
| I.a.48. | —CHNNH(CO)NHCH$_2$CF$_3$ | —OCH$_3$ | 1.085 | 386 | |
| I.a.49. | —CHNNH(CO)NHCH$_2$CH$_3$ | —OCH$_3$ | 1.029 | 332 | |
| I.a.50. | —CHNNH(CO)NHCH$_2$CF$_3$ | —OH | 0.980 | 372 | |
| I.a.51. | —CHNNH(CO)NHCH$_2$CH$_3$ | —OH | 0.905 | 318 | |
| I.a.52. | —CHNOCH$_3$ | —OCH$_3$ | 1.157 | 276 | |
| I.a.53. | —CH$_2$O(CO)CH$_3$ | —OH | 2.686 | 277 | 220 |
| I.a.54. | —CHNOH | —OH | 0.839 | 248 | |
| I.a.55. | —CHNOCH$_3$ | —OH | 0.963 | 262 | |
| I.a.56. | —NHC$_6$H$_5$ | —OH | 3.349 | 296 | 50.5 |
| I.a.57. | —NHC$_6$H$_5$ | —SCH$_3$ | 4.183 | 326 | 192 |
| I.a.58. | (N-cyclopropyl group, structure) | —OH | 2.500 | 260 | |
| I.a.59. | —(CH$_2$)$_2$CHNOCH$_3$ | —OH | 2.825 | 290 | |
| I.a.60. | —(CH$_2$)$_2$CHNNH(CO)NHCH$_2$CF$_3$ | —OH | 2.856 | 400 | |
| I.a.61. | —(CH$_2$)$_2$CHNNH(CO)NHCH$_2$CH$_3$ | —OH | 2.570 | 346 | |
| I.a.62. | —(CH$_2$)$_2$(CO)CH$_2$CH$_3$ | —OH | 2.708 | 289 | 120 |
| I.a.63. | —CH$_2$CHNOCH$_3$ | —OH | 2.743 | 276 | |
| I.a.64. | —CH$_2$CHNOH | —OH | 0.846 | 262 | |
| I.a.65. | (O-cyclohexyl group, structure) | —OH | | | |
| I.a.66. | —OCH$_2$C$_6$H$_5$ | —OH | 1.179 | 311 | |
| I.a.67. | —O(CH$_2$)$_2$OCH$_3$ | —OH | 0.970 | 279 | |
| I.a.68. | —CHO | —OCH$_2$CH$_3$ | | | |
| I.a.69. | —CH$_2$CHO | —OCH$_2$CH$_3$ | | | |
| I.a.70. | —(CH$_2$)$_2$CHO | —OCH$_2$CH$_3$ | | | |
| I.a.71. | —OCH$_2$CCH | —OCH$_2$CH$_3$ | 1.196 | 287 | |
| I.a.72. | —(CH$_2$)$_2$C(CH$_2$CH$_3$)NOCH$_3$ | —OCH$_2$CH$_3$ | 1.348, 1.385 (E/Z) | 346 | |

TABLE 3-continued

| | | | | | |
|---|---|---|---|---|---|
| I.a.73. | —(CH$_2$)$_2$C(CH$_2$CH$_3$)NOH | —OCH$_2$CH$_3$ | 1.173, 1.197 (E/Z) | 332 | |
| I.a.74. | —(CH$_2$)$_2$(CO)CH$_2$CH$_3$ | —OH | 1.014 | 289 | |
| I.a.75. | —CH$_2$C(CH$_2$CH$_3$)NOH | —OH | 0.925 | 290 | |
| I.a.76. | —CH$_2$C(CH$_2$CH$_3$)NOH | —OCH$_2$CH$_3$ | 1.121 | 318 | |
| I.a.77. | —CH$_2$(CO)CH$_2$CH$_3$ | —OCH$_2$CH$_3$ | 1.215 | 303 | |
| I.a.78. | —CH$_2$(CO)CH$_2$CH$_3$ | —OH | 0.682 | 275 | |
| I.a.79. | —(CH$_2$)$_2$C(CH$_2$CH$_3$)NOH (as E/Z mixture) | —OH | 0.952 and 0.981 | 304 | 201 |
| I.a.80. | —(CH$_2$)$_2$C(CH$_2$CH$_3$)NOCH$_3$ (as E/Z mixture) | —OH | 1.092 and 1.129 | 318 | 154 |
| I.a.81. | —(CH$_2$)$_2$C(CH$_2$CH$_3$)NNH$_2$ | —OH | 0.961 | 303 | 116 |
| I.a.82. | —OCH$_2$CCH | —OH | | | 186 |
| I.a.83. | —S-(4-CF$_3$—C$_6$H$_4$) | —OH | 3.780 | 381 | 222 |
| I.a.84. | —SC$_6$H$_5$ | —OH | 1.127 | 313 | 195 |
| I.a.85. | —SCH$_2$C$_6$H$_5$ | —OH | 1.196 | 327 | 163 |
| I.a.86. | —S-cyclohexyl | —OH | 1.275 | 319 | 148 |
| I.a.87. | —S-cyclopentyl | —OH | 1.210 | 305 | 143 |
| I.a.88. | —O-(2-chlorocyclohexyl) | —OH | 1.148 | 337 | 136 |
| I.a.89. | —O-(oxetan-3-yl) | —OH | 0.884 | 277 | 128 |
| I.a.90. | —O—C(CH$_3$)$_2$-cyclopropyl | —OH | | | 181 |
| I.a.91. | —O-cyclopentyl | —OH | 1.118 | 289 | 145 |
| I.a.92. | —O-cyclobutyl | —OH | 1.059 | 275 | 158 |
| I.a.93. | —OCH$_2$-cyclopropyl | —OH | 1.051 | 275 | 151 |

TABLE 3-continued

| cpd.-no | $^1$HNMR |
|---|---|
| I.a.46 | $(CD_3)_2CO$: σ = 7.99 (s, 1H); 7.93-7.95 (m, 2H); 7.63 (t, 2H); 7.47 (t, 1H); 2.50-2.60 (m, 1H); 1.22-1.33 (m, 4H); |
| I.a.65 | CDCl3: σ = 7.84 (s, 1H); 5.08-5.15 (m, 1H); 2.11-2.27 (m, 3H); 1.71-1.82 (m, 4H); 1.35-1.68 (m, 4H); 1.18-1.31 (m, 4H) |
| I.a.68 | $CDCl_3$: δ = 10.42 (s, 1H), 7.65 (s, 1H), 4.88 (q, J = 7.2 Hz, 2H), 2.2~2.3 (m, 1H), 1.40 (t, J = 7.2 Hz, 3H), 1.20~1.30 (m, 4H) |
| I.a.69 | CDCl3: δ = 9.87 (s, 1H), 7.72 (s, 1H), 4.41 (q, J = 7.2 Hz, 2H), 3.45 (s, 1H), 2.23 (m, 1H), 1.40 (t, J = 7.2 Hz, 3H), 1.16~1.28 (m, 4H) |
| I.a.70 | CDCl3: δ = 9.92 (s, 1H), 7.71 (s, 1H), 4.48 (q, J = 7.2 Hz, 2H), 3.48 (t, J = 7.2 Hz, 2H), 3.06 (t, J = 7.2 Hz, 2H), 2.24 (m, 1H), 1.47 (t, J = 7.2 Hz, 3H), 1.16~1.27 (m, 4H). |
| I.a.82 | (CD3)Cl3: σ = 7.79 (s, 1H); 5.13 (s, 2H); 2.66 (s, 1H); 2.20-2.30 (m, 1H); 1.17-1.36 (m, 4H); |
| I.a.84 | (CD3)2SO: σ = 7.85 (s, 1H); 7.64-7.73 (m, 2H); 7.43-7.52 (m, 3H); 2.40-2.55 (m, 1H); 1.00-1.25 (m, 4H); |
| I.a.87 | (CD3)2SO: σ = 7.79 (s, 1H); 3.91 (quintet, 1H); 2-40-2.50 (m, 1H); 2.18-2.30 (m, 2H); 1.55-1.80 (m, 6H); 1.08-1.21 (m, 4H); |
| I.a.89 | (CD3)Cl3: σ = 7.75 (s, 1H); 5.68 (t, 1H); 5.05-5.16 (m, 2H); 4.86-4.93 (m, 2H); 2.21-2.30 (m, 1H); 1.18-1.35 (m, 4H); |
| I.a.90 | (CD3)Cl3: σ = 7.90 (s, 1H); 2.25-2.32 (m, 1H); 1.63 (s, 6H); 1.49-1.60 (m, 1H); 1.21-1.30 (m, 4H); 0.50-0.62 (m, 4H); |
| I.a.92 | (CD3)Cl3: σ = 7.80 (s, 1H); 5.21 (quintet, 1H); 2-52-2.70 (m, 1H); 2.20-2.38 (m, 4H); 1.87-2.00 (q, 1H); 1.65-1.80 (m, 1H); 1.17-1.38 (m, 4H); |
| I.a.93 | (CD3)Cl3: σ = 7.82 (s, 1H); 4.37-4.45 (d, 2H); 2.21-2.30 (m, 1H); 1.37-1.51 (m, 1H); 1.13-1.30 (m, 4H); 0.65-0.78 (m, 2H); 0.45-0.52 (m, 2H); |

Use Examples

The herbicidal activity of the isoxazolo[5,4-b]pyridines of formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 80 and a very good herbicidal activity is given at values of at least 90.

The plants used in the greenhouse experiments belonged to the following species:

| Bayer Code | Scientific name | Common name |
| --- | --- | --- |
| ABUTH | *Abutilon theophrasti* | velvetleaf |
| AMARE | *Amaranthus retroflexus* L. | pigweed |
| CHEAL | *Chenopodium album* | fat-hen |
| SETFA | *Setaria faberi* | giant foxtail |
| SETVI | *Setaria viridis* | green foxtail |
| POLCO | *Polygonum convolvulus* | wild buckwheat |
| ECHCG | *Echinochloa crus-galli* | barnyard grass |

TABLE 4

Post-emergence treatment of *Abutilon theophrasti* (velvetleaf)

| cpd. no. | application rate [kg/ha] | damage [%] |
| --- | --- | --- |
| I.a.40 | 1000 | 100 |

TABLE 5

Post-emergence treatment of *Amaranthus retroflexus* L. (pigweed)

| cpd. no. | aplication rate [kg/ha] | damage [%] |
| --- | --- | --- |
| I.a.1 | 500 | 100 |
| I.a.59 | 500 | 98 |
| I.a.74 | 500 | 98 |
| I.a.44 | 1000 | 100 |
| I.a.66 | 1000 | 100 |
| I.a.79 | 500 | 100 |

TABLE 5-continued

Post-emergence treatment of *Amaranthus retroflexus* L. (pigweed)

| cpd. no. | aplication rate [kg/ha] | damage [%] |
| --- | --- | --- |
| I.a.80 | 500 | 100 |
| I.a.82 | 500 | 100 |
| I.a.86 | 500 | 95 |
| I.a.87 | 500 | 80 |
| I.a.88 | 500 | 100 |
| I.a.89 | 500 | 70 |
| I.a.91 | 500 | 100 |
| I.a.92 | 500 | 100 |
| I.a.93 | 500 | 100 |

TABLE 6

Post-emergence treatment of *Chenopodium album* (fat-hen)

| cpd. no. | application rate [kg/ha] | damage [%] |
| --- | --- | --- |
| I.a.37 | 1000 | 100 |
| I.a.1 | 500 | 100 |
| I.a.59 | 500 | 98 |
| I.a.74 | 500 | 98 |
| I.a.44 | 1000 | 100 |
| I.a.46 | 1000 | 100 |
| I.a.67 | 1000 | 100 |
| I.a.66 | 1000 | 100 |
| I.a.80 | 500 | 98 |
| I.a.81 | 500 | 75 |
| I.a.87 | 500 | 70 |
| I.a.88 | 500 | 100 |
| I.a.89 | 500 | 70 |
| I.a.91 | 500 | 98 |
| I.a.92 | 500 | 100 |
| I.a.93 | 500 | 100 |

TABLE 7

Post-emergence treatment of *Setaria faberi* (giant foxtail)

| cpd. no. | application rate [kg/ha] | damage [%] |
| --- | --- | --- |
| I.a.40 | 1000 | 85 |

TABLE 8

Post-emergence treatment of *Polygonum convolvulus* (wild buckwheat)

| cpd. no. | application rate [kg/ha] | damage [%] |
| --- | --- | --- |
| I.a.37 | 1000 | 100 |
| I.a.60 | 500 | 95 |
| I.a.67 | 1000 | 98 |
| I.a.79 | 500 | 85 |
| I.a.80 | 500 | 100 |
| I.a.93 | 500 | 100 |

TABLE 9

Post-emergence treatment of *Echinochloa crus-galli* (barnyard grass)

| cpd. no. | application rate [kg/ha] | damage [%] |
| --- | --- | --- |
| I.a.85 | 500 | 70 |
| I.a.87 | 500 | 75 |

TABLE 10

| Post-emergence treatment of Setaria viridis (green foxtail) | | |
|---|---|---|
| cpd. no. | application rate [kg/ha] | damage [%] |
| I.a.92 | 500 | 85 |

The invention claimed is:
1. An isoxazolo[5,4-b]pyridine compound of formula I

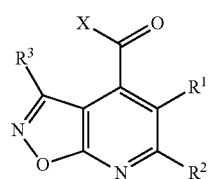

or the agriculturally useful salts of isoxazolo[5,4-b]pyridine compounds of formula I, wherein in formula I, the variables are as defined below:
$R^1$ is selected from the group consisting of hydrogen, halogen, hydroxyl, $C_1$-$C_6$-alkyl, $C_1$-$C_6$-haloalkyl, $C_1$-$C_6$-alkoxy-$C_1$-$C_6$-alkyl, $C_3$-$C_6$-cycloalkyl, $C_3$-$C_6$-halocycloalkyl, $C_2$-$C_6$-alkenyl, $C_2$-$C_6$-alkynyl, $C_1$-$C_6$-alkoxy, $C_1$-$C_6$-haloalkoxy, phenyl, and phenyl-$C_1$-$C_6$-alkyl;
$R^2$ is selected from the group consisting of hydrogen, $C_1$-$C_6$-alkyl, $C_1$-$C_6$-haloalkyl, $C_1$-$C_6$-hydroxyalkyl, $C_1$-$C_6$-alkoxy-$C_1$-$C_6$-alkyl, $C_3$-$C_6$-cycloalkyl, $C_3$-$C_6$-halocycloalkyl, $C_1$-$C_6$-alkyl-$C_3$-$C_6$-cycloalkyl, phenyl-$C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkylthio, amino, $C_1$-$C_6$-alkylamino, N,N-di-($C_1$-$C_6$-alkyl)amino, and heterocyclyl, phenyl; wherein the heterocyclyl and phenyl moieties of $R^2$ can be unsubstituted or substituted with one or more radicals selected from the group consisting of halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, and heterocyclyl, phenyl;
or $R^1$ and $R^2$ together form an $C_3$-$C_5$-alkanediyl;
R3 is selected from the group consisting of $C_3$-$C_6$-cycloalkyloxy-$C_1$-$C_6$-alkyl-, $C_3$-$C_6$-halocycloalkyloxy-$C_1$-$C_6$-alkyl-, phenoxy-$C_1$-$C_6$-alkyl-, heterocyclyloxy-$C_1$-$C_6$-alkyl-, phenyl-$C_1$-$C_6$-alkoxyl-$C_1$-$C_6$-alkyl, $C_1$-$C_6$-alkyl-carbonyloxy-$C_1$-$C_6$-alkyl-, amino-$C_1$-$C_6$-alkyl-, ($C_1$-$C_6$-alkyl)amino-$C_1$-$C_6$-alkyl-, N,N-di-($C_1$-$C_6$-alkyl)amino-$C_1$-$C_6$-alkyl-, ($C_3$-$C_6$-cycloalkyl)amino-$C_1$-$C_6$-alkyl-, N,N-di-($C_3$-$C_6$-cycloalkyl)amino-$C_1$-$C_6$-alkyl-, [N—($C_1$-$C_6$-alkyl),N—($C_3$-$C_6$-cycloalkyl)]amino-$C_1$-$C_6$-alkyl-, $C_1$-$C_6$-alkyl-carbonyl-$C_1$-$C_6$-alkyl-, $C_1$-$C_6$-alkoxy-$C_1$-$C_6$-haloalkyl-, $C_1$-$C_6$-haloalkoxy-$C_1$-$C_6$-haloalkyl-, $C_1$-$C_6$-alkoxy-$C_1$-$C_6$-alkoxy-$C_1$-$C_6$-alkyl-, formyl-, formyl-$C_1$-$C_6$-alkyl-, $C_1$-$C_6$-alkyl-carbonyl-, $C_3$-$C_6$-cycloalkyloxy-, $C_3$-$C_6$-halocycloalkyloxy-, $C_1$-$C_6$-alkyl-$C_3$-$C_6$-cycloalkyloxy-, $C_1$-$C_6$-alkyl-$C_3$-$C_6$-halocycloalkyloxy-, $C_1$-$C_6$-haloalkyl-$C_3$-$C_6$-cycloalkyloxy-, $C_1$-$C_6$-haloalkyl-$C_3$-$C_6$-halocycloalkyloxy-, $C_3$-$C_6$-cycloalkyl-$C_1$-$C_6$-alkoxy-, $C_3$-$C_6$-halocycloalkyl-$C_1$-$C_6$-alkoxy-, $C_3$-$C_6$-cycloalkyl-$C_1$-$C_6$-haloalkoxy-, $C_3$-$C_6$-halocycloalkyl-$C_1$-$C_6$-haloalkoxy-, $C_3$-$C_6$-alkenyloxy-, $C_3$-$C_6$-haloalkenyloxy-, $C_3$-$C_6$-alkynyloxy-, $C_3$-$C_6$-haloalkynyloxy-, $C_1$-$C_6$-alkoxy-$C_1$-$C_6$-alkoxy-, phenyl-$C_1$-$C_6$-alkoxy-, phenyl-$C_1$-$C_6$-haloalkoxy-, heterocyclyl-$C_1$-$C_6$-alkoxy-, heterocyclyl-$C_1$-$C_6$-haloalkoxy, phenoxy-, heterocyclyloxy-, phenylcarbonyloxy-, heterocyclylcarbonyloxy-, $C_3$-$C_6$-cycloalkylthio-, $C_3$-$C_6$-halocycloalkylthio-, $C_3$-$C_6$-cycloalkyl-$C_1$-$C_6$-alkylthio-, $C_3$-$C_6$-halocycloalkyl-$C_1$-$C_6$-alkylthio-, $C_3$-$C_6$-cycloalkyl-$C_1$-$C_6$-haloalkylthio-, $C_3$-$C_6$-halocycloalkyl-$C_1$-$C_6$-haloalkylthio-, heterocyclylthio-, phenylthio-, phenyl-$C_1$-$C_6$-alkylthio-, heterocyclyl-$C_1$-$C_6$-alkylthio-, $C_1$-$C_6$-alkylsulfonyl-, $C_1$-$C_6$-haloalkylsulfonyl-, $C_3$-$C_6$-cycloalkylsulfonyl-, $C_3$-$C_6$-halocycloalkylsulfonyl-, heterocyclylsulfonyl-, phenylsulfonyl-, phenyl-$C_1$-$C_6$-alkylsulfonyl-, heterocyclyl-, $C_1$-$C_6$-alkylsulfonyl-, $C_1$-$C_6$-alkylsulfinyl-, $C_1$-$C_6$-haloalkylsulfinyl-, $C_3$-$C_6$-cycloalkylsulfinyl-, $C_3$-$C_6$-halocycloalkylsulfinyl-, heterocyclylsulfinyl-, phenylsulfinyl-, phenyl-$C_1$-$C_6$-alkylsulfinyl-, heterocyclyl-$C_1$-$C_6$-alkylsulfinyl-, phenylamino-, heterocyclylamino-, [N—($C_1$-$C_6$-alkyl),N-phenyl]amino-, [N—($C_1$-$C_6$-alkyl),N—($C_3$-$C_6$-cycloalkyl)]amino-, N—($C_3$-$C_6$-cycloalkyl)amino-, N,N-di-($C_3$-$C_6$-cycloalkyl)amino-, [N—($C_1$-$C_6$-alkyl),N—($C_3$-$C_6$-halocycloalkyl)]amino-, [N—($C_1$-$C_6$-alkyl),N—($C_1$-$C_6$-haloalkyl)]amino-, ($C_3$-$C_6$-halocycloalkyl)amino-, N,N-di-($C_3$-$C_6$-halocycloalkyl)amino, [N—($C_1$-$C_6$-alkyl),N-(phenyl-$C_1$-$C_6$-alkyl)]amino-, (phenyl-$C_1$-$C_6$-alkyl)amino-, (heterocyclyl-$C_1$-$C_6$-alkyl)amino-, N—[($C_3$-$C_6$-cycloalkyl)-($C_1$-$C_6$-alkyl)]amino-, N,N-di-[($C_3$-$C_6$-cycloalkyl)-($C_1$-$C_6$-alkyl)]amino-, N—[($C_3$-$C_6$-halocycloalkyl)-($C_1$-$C_6$-alkyl)]amino-, and N—($C_1$-$C_6$-alkyl)-N—[($C_3$-$C_6$-cycloalkyl)-($C_1$-$C_6$-alkyl)]amino-, wherein the heterocyclyl and phenyl moieties of $R^3$ can be unsubstituted or substituted with one or more radicals selected from the group consisting of halogen, hydroxy, nitro, cyano, $C_1$-$C_6$-alkyl, $C_1$-$C_6$-haloalkyl, $C_1$-$C_6$-alkoxy-$C_1$-$C_6$-alkyl-, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy-, $C_1$-$C_6$-alkoxycarbonyl-, $C_1$-$C_6$-alkylthio, $C_1$-$C_6$-alkylsulfinyl-, $C_1$-$C_6$-alkylsulfonyl, amino, $C_1$-$C_6$-alkylamino, N,N-di-($C_1$-$C_6$-alkyl)amino, heterocyclyl, phenyl, and the moiety of formula II,

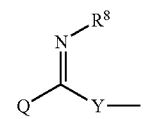

wherein
Q is hydrogen or $C_1$-$C_6$-alkyl;
Y is a direct bond or $C_1$-$C_6$-alkanediyl;
$R^e$ is selected from the group consisting of amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino]-, and $C_1$-$C_6$-haloalkyl-[(aminocarbonyl)amino];
X is selected from the group consisting of $OR^4$, $SR^5$; $NR^6R^7$;
$R^4$, $R^5$ are selected from the group consisting of hydrogen, $C_1$-$C_6$-alkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl-, $C_1$-$C_6$-alkoxy-$C_1$-$C_6$-alkoxy-$C_1$-$C_6$-alkyl-, $C_1$-$C_6$-haloalkoxy-$C_1$-$C_6$-alkyl-, $C_2$-$C_6$-alkenyloxy-$C_1$-$C_6$-alkyl-, $C_2$-$C_6$-haloalkenyloxy-$C_1$-$C_6$-alkyl-, $C_1$-$C_6$-alkoxycarbonyl-$C_1$-$C_6$-alkyl-, aminocarbonyl-$C_1$-$C_6$-alkyl-, $C_1$-$C_6$-alkyl-aminocarbonyl-$C_1$-$C_6$-alkyl-, N,N-di-($C_1$-$C_6$-alkyl)-aminocarbonyl-$C_1$-$C_6$-alkyl-, [N—($C_3$-$C_6$-cycloalkyl-$C_1$-$C_6$-alkyl), N—($C_1$-$C_6$-ALKYL)]-AMINOCARBONYL-$C_1$-$C_6$-ALKYL, $C_1$-$C_6$-ALKOXY-AMINOCARBONYL-$C_1$-$C_6$-ALKYL-, $C_2$-$C_6$-alkenyl, $C_2$-$C_6$-haloalkenyl, $C_2$-$C_6$-alkynyl-$C_2$-$C_6$-alkenyl-, $C_3$-$C_6$-alkynyl, $C_3$-$C_6$-haloalkynyl, heterocyclyl, phenyl, heterocyclylcarbonyl-, phenylcarbonyl-, heterocyclylcarbonyl-C1-C6-alkyl-, phenylcarbonyl-$C_1$-$C_6$-alkyl-, heterocyclyl-$C_1$-$C_6$-alkyl-, and phenyl-$C_1$-$C_6$-alkyl-; wherein the phenyl and heterocyclyl moieties of $R^4$ and $R^5$ can be unsubstituted or substituted with one or more radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxycarbonyl, heterocyclyl, phenyl;

$R^6$, $R^7$ is selected from the group consisting of hydrogen, $C_1$-$C_6$-alkyl, and $C_1$-$C_6$-haloalkyl.

2. The compound of claim 1, wherein in formula I $R^1$ is selected from the group consisting of hydrogen, halogen, $C_1$-$C_6$-alkyl, and $C_1$-$C_6$-haloalkyl.

3. The compound of claim 1, wherein in formula I $R^1$ is hydrogen.

4. The compound of claim 1, wherein in formula I $R^2$ is selected from the group consisting of $C_1$-$C_6$-alkyl, $C_1$-$C_6$-haloalkyl, $C_1$-$C_6$-hydroxyalkyl, $C_3$-$C_6$-cycloalkyl, $C_3$-$C_6$-halocycloalkyl, $C_2$-$C_6$-alkenyl, and $C_2$-$C_6$-alkynyl.

5. The compound of claim 1, wherein in formula I $R^2$ is $C_3$-$C_6$-cycloalkyl, $C_3$-$C_6$-halocycloalkyl.

6. The compound of claim 1, wherein in formula I R3 is selected from the group consisting of $C_3$-$C_6$-cycloalkyloxy-$C_1$-$C_6$-alkyl-, $C_3$-$C_6$-halocycloalkyloxy-$C_1$-$C_6$-alkyl-, phenoxy-$C_1$-$C_6$-alkyl-, heterocycyloxy-$C_1$-$C_6$-alkyl-, phenyl-$C_1$-$C_6$-alkoxy-$C_1$-$C_6$-alkyl-, $C_1$-$C_6$-alkyl-carbonyloxy-$C_1$-$C_6$-alkyl-, amino-$C_1$-$C_6$-alkyl-, ($C_1$-$C_6$-alkyl)amino-$C_1$-$C_6$-alkyl-, N,N-di-($C_1$-$C_6$-alkyl)amino-$C_1$-$C_6$-alkyl, ($C_3$-$C_6$-cycloalkyl)amino-$C_1$-$C_6$-alkyl-, N,N-di-($C_3$-$C_6$-cycloalkyl)amino-$C_1$-$C_6$-alkyl, [N—($C_1$-$C_6$-alkyl),N—($C_3$-$C_6$-cycloalkyl)]amino-$C_1$-$C_6$-alkyl-, $C_1$-$C_6$-alkyl-carbonyl-$C_1$-$C_6$-alkyl-, $C_1$-$C_6$-alkoxy-$C_1$-$C_6$-haloalkyl-, $C_1$C-aoloyC_1C-aoly_$C_1$-$C_6$-alkoxy-$C_1$-$C_6$-alkoxy-$C_1$-$C_6$-alkyl-, formyl, formyl-$C_1$-$C_6$-alkyl-, $C_1$-$C_6$-alkyl-carbonyl-, $C_3$-$C_6$-cycloalkyloxy-, $C_3$-$C_6$-halocycloalkyloxy-, $C_1$-$C_6$-alkyl-$C_3$-$C_6$-cycloalkyloxy-, $C_1$-$C_6$-alkyl-$C_3$-$C_6$-halocycloalkyloxy-, $C_1$-$C_6$-haloalkyl-$C_3$-$C_6$-cycloalkyloxy, $C_1$-$C_6$-haloalkyl-$C_3$-$C_6$-halocycloalkyloxy-, $C_1$-$C_6$-cycloalkyl-$C_1$-$C_6$-alkoxy-, $C_3$-$C_6$-halocycloalkyl-$C_1$-$C_6$-alkoxy-, $C_3$-$C_6$-cycloalkyl-$C_1$-$C_6$-haloalkoxy-, $C_3$-$C_6$-halocycloalkyl-$C_1$-$C_6$-haloalkoxy-, $C_3$-$C_6$-alkenyloxy-, $C_3$-$C_6$-haloalkenyloxy-, $C_3$-$C_6$-alkynyloxy-, $C_3$-$C_6$-haloalkynyloxy, $C_1$-$C_6$-alkoxy-$C_1$-$C_6$-alkoxy-, phenyl-$C_1$-$C_6$-alkoxy-, phenyl-$C_1$-$C_6$-haloalkoxy-, heterocyclyl-$C_1$-$C_6$-alkoxy-, heterocyclyl-$C_1$-$C_6$-haloalkoxy-, phenoxy-, heterocyclyloxy-, phenylcarbonyloxy-, heterocyclylcarbonyloxy-, $C_3$-$C_6$-cycloalkylthio-, $C_3$-$C_6$-halocycloalkylthio-, $C_3$-$C_6$-cycloalkyl-$C_1$-$C_6$-alkylthio-, $C_3$-$C_6$-halocycloalkyl-$C_1$-$C_6$-alkylthio-, C3-C6-cycloakyl-$C_1$-$C_6$-haloalkylthio-, C3-C6-halocycloalkyl-$C_1$-$C_6$-haloalkylthio-, heterocyclylthio-, phenylthio-, phenyl-$C_1$-$C_6$-alkylthio-, heterocyclyl-$C_1$-$C_6$-alkylthio-, phenylamino-, heterocyclylamino-, [N—($C_1$-$C_6$-alkyl), N-phenyl]amino-, [N—($C_1$-$C_6$-alkyl),N—($C_3$-$C_6$-cycloalkyl)]amino-, N—($C_3$-$C_6$-cycloalkyl)amino-, N,N-di-($C_3$-$C_6$-cycloalkyl)amino-, [N—($C_1$-$C_6$-alkyl),N—($C_3$-$C_6$-halocycloalkyl)]amino-, [N—($C_1$-$C_6$-alkyl),N—($C_1$-$C_6$-haloalkyl)]amino-, ($C_3$-$C_6$-halocycloalkyl)amino-, N,N-di-($C_3$-$C_6$-halocycloalkyl)amino-, [N—($C_3$-$C_6$-cycloalkyl)amino-, N—($C_1$-$C_6$-alkyl), N-(phenyl-$C_1$-$C_6$-alkylamino-, (phenyl-$C_1$-$C_6$-alkyl)amino-, (heterocyclyl-$C_1$-$C_6$-alkyl)amino-, N—[($C_3$-$C_6$-cycloalkyl)-($C_1$-$C_6$-alkyl)]amino-, N,N-di-[($C_3$-$C_6$-cycloalkyl)-($C_1$-$C_6$-alkyl)]amino-, N—[($C_3$-$C_6$-halocycloalkyl)-($C_1$-$C_6$-alkyl)]amino-, N—($C_1$-$C_6$-alkyl)-N—[($C_3$-$C_6$-cycloalkyl)-($C_1$-$C_6$-alkyl)]amino-, wherein the heterocyclyl and phenyl moieties of $R^3$ can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl-, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylsulfinyl, $C_1$-$C_6$-alkylsulfonyl-, amino, $C_1$-$C_6$-alkylamino-, N,N-di-$C_1$-$C_6$-alkyl)amino-, heterocyclyl, phenyl, and the moiety of formula II, (II)

wherein

Q is hydrogen or $C_1$-$C_6$-alkyl;

Y is a direct bond or $C_1$-$C_6$-alkanediyl;

$R^3$ is selected from the group consisting of amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino]-, and $C_1$-$C_6$-haloalkyl-[(aminocarbonyl)amino]-.

7. The compound of claim 1, wherein in formula I $R^3$ is selected from the group consisting of $C_1$-$C_6$-alkyl-carbonyloxy-$C_1$-$C_6$-alkyl-, $C_1$-$C_6$-alkyl-carbonyl-$C_1$-$C_6$-alkyl-, formyl, formyl-$C_1$-$C_6$-alkyl-, C3-C6-cycloalkyloxy-, C3-C6-halocycloalkyloxy-, C3-C6-cycloalkyl-$C_1$-$C_6$-alkoxy-, C3-C6-alkenyloxy-, C3-$C_8$-alkynyloxy-, $C_1$-$C_6$-alkoxy-$C_1$-$C_6$-alkoxy-, phenyl-$C_1$-$C_6$-alkoxy-, phenoxy, heterocyclyloxy-, phenylcarbonyloxy-, C3-C6-cycloalkylthio-, phenylthio-, phenyl-$C_1$-$C_6$-alkylthio-, phenylamino-, N—($C_3$-$C_6$-cycloalkyl)amino-, N—[($C_3$-$C_6$-cycloalkyl)-($C_1$-$C_6$-alkyl)]amino-, wherein the phenyl moieties of $R^3$ can be unsubstituted or substituted with $C_1$-$C_6$-haloalkyl, and the moiety of formula II, (II)

wherein

Q is hydrogen or $C_1$-$C_6$-alkyl;

Y is a direct bond or $C_1$-$C_6$-alkanediyl;

$R^3$ is selected from the group consisting of amino, hydroxy, $C_1$-$C_6$-alkoxy, $C_1$-$C_6$-alkyl-[(aminocarbonyl)amino]-, and $C_1$-$C_6$-haloalkyl-[(aminocarbonyl)amino]-.

8. The compound of claim 1, wherein in formula I X is $OR^4$, $SR^5$.

9. The compound of claim 1, wherein in formula I
X is $OR^4$;
$R^4$ is selected from the group consisting of hydrogen, $C_1$-$C_6$-alkyl, $C_1$-$C_6$-haloalkyl, $C_1$-$C_6$-cyanoalkyl, $C_1$-$C_6$-alkoxy-$C_1$-$C_6$-alkyl-, $C_1$-$C_6$-haloalkoxy-$C_1$-$C_6$-alkyl-, $C_2$-C6-alkenyl, $C_2$-$C_6$-haloalkenyl, and $C_3$-$C_6$-alkynyl.

10. The compound of claim 1, wherein in formula I $R^4$ is hydrogen.

11. The compound of claim 1, wherein in formula I
X is $SR^5$;
$R^5$ is selected from the group consisting of hydrogen, $C_1$-$C_6$-alkyl, $C_1$-$C_6$-haloalkyl, phenyl-$C_1$-$C_6$-alkyl-, $C_2$-$C_6$-alkenyl, $C_2$-$C_6$-haloalkenyl, and $C_3$-$C_6$-alkynyl.

12. A composition comprising a herbicidally active amount of at least one isoxazolo[5,4-b]pyridine compound of formula I or an agriculturally useful salt of formula I as defined in claim 1, and auxiliaries customary for formulating crop protection agents.

13. A method for preparing the composition of claim 12, comprising mixing a herbicidally active amount of at least one isoxazolo[5,4-b]pyridine compound of formula I or an agriculturally useful salt of formula I and auxiliaries customary for formulating crop protection agents.

14. A method for controlling unwanted vegetation, comprising allowing a herbicidally effective amount of at least one isoxazolo[5,4-b]pyridine compound of formula I or an agriculturally useful salt of I as defined in claim 1 to act on plants, their seeds and/or their habitat.

15. A method for controlling unwanted vegetation, comprising allowing a herbicidally effective amount of the composition of claim 12 to act on plants, their seeds and/or their habitat.

16. The method of claim 14, wherein in formula I X is $OR^4$, $SR^5$.

17. The method of claim 14, wherein in formula I
X is $OR^4$;
$R^4$ is selected from the group consisting of hydrogen, $C_1$-$C_6$-alkyl, $C_1$-$C_6$-haloalkyl, $C_1$-$C_6$-cyanoalkyl, $C_1$-$C_6$-alkoxy-$C_1$-$C_6$-alkyl-, $C_1$-$C_6$-haloalkoxy-$C_1$-$C_6$-alkyl-, $C_2$-C6-alkenyl, $C_2$-$C_6$-haloalkenyl, and $C_3$-$C_6$-alkynyl.

18. The method of claim 14, wherein in formula I $R^4$ is hydrogen.

19. The method of claim 14, wherein in formula I
X is $SR^5$;
$R^5$ is selected from the group consisting of hydrogen, $C_1$-$C_6$-alkyl, $C_1$-$C_6$-haloalkyl, phenyl-$C_1$-$C_6$-alkyl-, $C_2$-$C_6$-alkenyl, $C_2$-$C_6$-haloalkenyl, and $C_3$-$C_6$-alkynyl.

20. The method of claim 14, wherein in formula I $R^2$ is $C_3$-$C_6$-cycloalkyl, $C_3$-$C_6$-halocycloalkyl.

21. The method of claim 14, wherein in formula I
$R^6$ is selected from the group consisting of C3-C6-cycloalkyloxy-$C_1$-$C_6$-alkyl, C3-C6-halocycloalkyloxy-$C_1$-$C_6$-alkyl-, phenoxy-$C_1$-$C_6$-alkyl, heterocyclyloxy-$C_1$-$C_6$-alkyl-, phenyl-$C_1$-$C_6$-alkoxy-$C_1$-$C_6$-alkyl-, $C_1$-$C_6$-alkyl-carbonyloxy-$C_1$-$C_6$-alkyl-, amino-$C_1$-$C_6$-alkyl-, ($C_1$-$C_6$-alkyl)amino-$C_1$-$C_6$-alkyl-, N,N-di-($C_1$-$C_6$-alkyl)amino-$C_1$-$C_6$-alkyl-, ($C_3$-$C_6$-cycloalkyl)amino-$C_1$-$C_6$-alkyl-, N,N-di-($C_3$-$C_6$-cycloalkyl)amino-$C_1$-$C_6$-alkyl, [N—($C_1$-$C_6$-alkyl),N(C3-C6-cycloalkyl)]amino-$C_1$-$C_6$-alkyl-, $C_1$-$C_6$-alkyl-carbonyl-$C_1$-$C_6$-alkyl-, $C_1$-$C_6$-alkoxy-$C_1$-$C_6$-haloalkyl-, $C_1$-$C_6$-haloalkoxy-$C_1$-$C_6$-haloalkyl-, $C_1$-$C_6$-alkoxy-$C_1$-$C_6$-alkoxy-$C_1$-$C_6$-alkyl-, formyl, formyl-$C_1$-$C_6$-alkyl-, $C_1$-$C_6$-alkyl-carbonyl-, C3-C6-cycloalkyloxy-, C3-C6-halocycloalkyloxy-, $C_1$-$C_6$-alkyl-C3-C6-cycloalkyloxy, $C_1$-$C_6$-alkyl-C3-C6-halocycloalkyloxy-, $C_1$-$C_6$-haloalkyl-C3-C6-cycloalkyloxy, $C_1$-$C_6$-haloalkyl-C3-C6-halocycloalkyloxy-, C3-C6-cycloalkyl-$C_1$-$C_6$-alkoxy-, C3-C6-halocycloalkyl-$C_1$-$C_6$-alkoxy, C3-C6-cycloalkyl-$C_1$-$C_6$-haloalkoxy, C3-C6-halocycloalkyl-$C_1$-$C_6$-haloalkoxy, C3-C6-alkenyloxy-, C3-C6-haloalkenyloxy-, C3-C6-alkynyloxy-, C3-C6-haloalkynyloxy-, $C_1$-$C_6$-alkoxy-$C_1$-$C_6$-alkoxy-, phenyl-$C_1$-$C_6$-alkoxy-, phenyl-$C_1$-$C_6$-haloalkoxy-, heterocyclyl-$C_1$-$C_6$-alkoxy-, heterocyclyl-$C_1$-$C_6$-haloalkoxy-, phenoxy-, heterocyclyloxy-, phenylcarbonyloxy-, heterocyclylcarbonyloxy-, C3-C6-cycloalkylthio, C3-C6-halocycloalkylthio-, C3-C6-cycloalkyl-$C_1$-$C_6$-alkylthio-, C3-C6-halocycloalkyl-$C_1$-$C_6$-alkylthio-, C3-C6-cycloalkyl-$C_1$-$C_6$-haloalkylthio-, C3-C6-halocycloalkyl-$C_1$-$C_6$-haloalkylthio-, heterocyclylthio-, phenylthio-, phenyl-$C_1$-$C_6$-alkylthio-, heterocyclyl-$C_1$-$C_6$-alkylthio-, phenylamino-, heterocyclylamino-, [N—($C_1$-$C_6$-alkyl),N-phenyl]amino-, [N—($C_1$-$C_6$-alkyl),N—(C3-C6-cycloalkyl)]amino-, N—(C3-$C_6$-cycloalkyl)amino-, N,N-di-($C_3$-$C_6$-cycloalkyl)amino-, [N—($C_1$-$C_6$-alkyl),N—(C3-$C_6$-halocycloalkyl)]amino-, [N—($C_1$-$C_6$-alkyl),N—($C_1$-$C_6$-haloalkyl)]amino-, ($C_3$-$C_6$-halocycloalkyl)amino-, N,N-di-($C_3$-$C_6$-halocycloalkyl)amino-, [N—($C_1$-$C_6$-alkyl),N-(phenyl-$C_1$-$C_6$-alkyl)]amino-, (phenyl-$C_1$-$C_6$-alkyl)amino-, (heterocyclyl-$C_1$-$C_6$-alkyl)amino-, N—[(C3-C6-cycloalkyl)-($C_1$-$C_6$-alkyl)]amino-, N,N-di-[(C3-C6-cycloalkyl)-($C_1$-$C_6$-alkyl)]amino-, N—[(C3-C6-halocycloalkyl)-($C_1$-$C_6$-alkyl)]amino-, N—($C_1$-$C_6$-alkyl)-N—[(C3-C6-cycloalkyl)-($C_1$-$C_6$-alkyl)]amino-, wherein the heterocyclyl and phenyl moieties of R, can be unsubstituted or substituted with one or more radicals selected from halogen, hydroxy, nitro, cyano, $C_1$-$C_6$-alkyl, $C_1$-$C_6$-haloalkyl, $C_1$-$C_6$-alkoxy-$C_1$-$C_6$-alkyl-, $C_3$-$C_6$-cycloalkyl, $C_2$-$C_6$-alkenyl, $C_1$-$C_6$-alkynyl, $C_1$-$C_6$-alkoxy, $C_1$-$C_6$-haloalkoxy, $C_1$-$C_6$-alkoxycarbonyl-, $C_1$-$C_6$-alkylthio, $C_1$-$C_6$-alkylsulfinyl, $C_1$-$C_6$-alkylsulfonyl, amino, $C_1$-$C_6$-alkylamino, N,N-di-($C_1$-$C_6$)amino, heterocyclyl, phenyl, and the moiety of formula II,

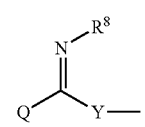

(II)

wherein
Q is hydrogen or $C_1$-$C_6$-alkyl;
Y is a direct bond or $C_1$-$C_6$-alkanediyl;
$R^8$ is selected from the group consisting of amino, $C_1$-$C_6$-alkylamino, di-$C_1$-$C_6$-alkylamino, $C_1$-$C_6$-alkyl, hydroxy, $C_1$-$C_6$-alkoxy, $C_1$-$C_6$-alkyl-[(aminocarbonyl)amino]-, and $C_1$-$C_6$-haloalkyl-[(aminocarbonyl)amino]-.

22. The method of claim 14, wherein in formula I
$R^3$ is selected from the group consisting of $C_1$-$C_6$-alkyl-carbonyloxy-$C_1$-$C_6$-alkyl-, $C_1$-$C_6$-alkyl-carbonyl-$C_1$-$C_6$-alkyl-, formyl, formyl-$C_1$-$C_6$-alkyl-, $C_3$-$C_6$-cycloalkyloxy-, $C_3$-$C_6$-halocycloalkyloxy-, $C_3$-$C_6$-cycloalkyl-$C_1$-$C_6$-alkoxy-, $C_3$-$C_6$-alkenyloxy-, $C_3$-$C_6$-alkynyloxy-, $C_1$-$C_6$-alkoxy-$C_1$-$C_6$-alkoxy-, phenyl-$C_1$-

$C_6$-alkoxy-, phenoxy-, heterocyclyloxy-, phenylcarbonyloxy-, $C_3$-$C_6$-cycloalkylthio-, phenylthio-, phenyl-$C_1$-$C_6$-alkylthio-, phenylamino-, N—($C_3$-$C_6$-cycloalkyl)amino-, N—[($C_3$-$C_6$-cycloalkyl)-($C_1$-$C_6$-alkyl)]amino-, wherein the phenyl moieties of $R^3$ can be unsubstituted or substituted with $C_1$-$C_6$-haloalkyl, and the moiety of formula II,

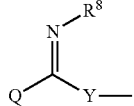
(II)

wherein

Q is hydrogen or $C_1$-$C_6$-alkyl;

Y is a direct bond or $C_1$-$C_6$-alkanediyl;

$R^6$ is selected from the group consisting of amino, hydroxy, $C_1$-$C_6$-alkoxy, $C_1$-$C_3$-alkyl-[(aminocarbonyl)amino]-, and $C_1$-$C_6$-haloalkyl-[(aminocarbonyl)amino]-.

* * * * *